US009986722B2

(12) United States Patent
Fogh et al.

(10) Patent No.: US 9,986,722 B2
(45) Date of Patent: Jun. 5, 2018

(54) ANIMAL MODEL OF KRABBE'S DISEASE

(71) Applicant: Chiesi Farmaceutici S.p.A., Parma (IT)

(72) Inventors: Jens Fogh, Lynge (DK); Claes Andersson, Täby (SE)

(73) Assignee: Chiesi Farmaceutici S.p.A., Parma (IT)

( * ) Notice: Subject to any disclaimer, the term of this patent is extended or adjusted under 35 U.S.C. 154(b) by 119 days.

(21) Appl. No.: 14/418,038

(22) PCT Filed: Aug. 7, 2013

(86) PCT No.: PCT/DK2013/050260
§ 371 (c)(1),
(2) Date: Jan. 28, 2015

(87) PCT Pub. No.: WO2014/023314
PCT Pub. Date: Feb. 13, 2014

(65) Prior Publication Data
US 2015/0196014 A1 Jul. 16, 2015

(30) Foreign Application Priority Data

Aug. 7, 2012 (DK) ................................ 2012 70467

(51) Int. Cl.
*A01K 67/027* (2006.01)
*C12N 9/24* (2006.01)
*A61K 49/00* (2006.01)
*C12N 15/85* (2006.01)

(52) U.S. Cl.
CPC ...... *A01K 67/0278* (2013.01); *A61K 49/0008* (2013.01); *C12N 9/2402* (2013.01); *C12N 15/8509* (2013.01); *A01K 2217/072* (2013.01); *A01K 2227/105* (2013.01); *A01K 2267/0318* (2013.01); *C12Y 302/01046* (2013.01)

(58) Field of Classification Search
CPC ........ A01K 2217/072; A01K 2227/105; A01K 67/0278; A01K 2267/0318; C12N 15/8509; C12N 9/2402; C12Y 302/01046; A61K 49/0008
See application file for complete search history.

(56) References Cited

FOREIGN PATENT DOCUMENTS

| JP | 1-149718 A | 6/1989 |
|----|------------|--------|
| WO | WO2002001950 A3 * | 2/2003 |
| WO | WO 2009/040816 A1 | 4/2009 |
| WO | WO 2011/163651 A2 | 12/2011 |

OTHER PUBLICATIONS

Luiz et al. "Generation of a mouse with low galactocerebrosidase activity by gene targeting: a new model of globoid cell leukodystrophy (Krabbe disease)." Mol Genet Metab. Jul. 2001;73(3):211-23.*
Polejaeva and Mitalipov S. "Stem cell potency and the ability to contribute to chimeric organisms." Reproduction. Mar. 7, 2013;145(3):R81-8.*
Brevini et al. "Porcine embryonic stem cells: Facts, challenges and hopes." Theriogenology. Sep. 1, 2007;68 Suppl 1:S206-13.*
Gerlaii R. "Gene-targeting studies of mammalian behavior: is it the mutation or the background genotype?" Trends Neurosci. May 1996;19(5):177-81.*
Ozato et al. Comment on "Gene disruption study reveals a nonredundant role for TRIM21/Ro52 in NF-kappa B-dependent cytokine expression in fibroblasts". J Immunol. Dec. 15, 2009;183(12):7619.*
Lusis et al. "The problem of passenger genes in transgenic mice." Arterioscler Thromb Vasc Biol. Oct. 2007;27(10):2100-3.*
Speakman et al. "The contribution of animal models to the study of obesity." Lab Anim. Oct. 2008;42(4):413-32.*
Malandrini et al. "Peripheral neuropathy in late-onset Krabbe disease: report of three cases." Neurol Sci. Jan. 2013;34(1):79-83.*
Deane et al. "Insights into Krabbe disease from structures of galactocerebrosidase." Proc Natl Acad Sci U S A. Sep. 13, 2011; 108(37): 15169-15173.*
Altschul, Stephen F. et al., "Basic Local Alignment Search Tool" J. Mol. Biol., 1990, pp. 403-410, vol. 215.
De Gasperi, R. et al., "Transgenic rescue of Krabbe disease in the twitcher mouse" Gene Therapy, 2004, pp. 1188-1194, vol. 11.
Furuya, H. et al., "Apr. 13, 2002—Adult onset globoid cell leukodystrophy (Krabbe disease): Analysis of galactosylceramidase cDNA from four Japanese patients" Demyelinating Diseases, other than Multiple Sclerosis, Journal of neurological Sciences, 1997, p. 228, vol. 150.
LePage, David F. et al., "Animal Models for Disease-Knockout, Knockin and Conditional Mutant Mice" Methods in Molecular Medicine, 2006, pp. 41-67, vol. 129.
Luzi, Paola et al., "Generation of a Mouse with Low Galactocerebrosidase Activity by Gene Targeting: A New Model of Globoid Cell Leukodystrophy (Krabbe Disease)" Molecular Genetics and Metabolism, 2001, pp. 211-223, vol. 73.
Maegawa, Gustavo et al., "A proposed cell-based high-throughput screening assay to identify potential small molecules agents for treatment of Krabbe disease" Molecular Genetics and Metabolism, 2011, pp. 827-828, vol. 102.
Malandrini, A. et al., "Peripheral neuropathy in late-onset Krabbe disease: report of three cases" Neurological Sciences, 2013, pp. 79-83, vol. 34.
Tappino, Barbara et al., "Identification and Characterization of 15 Novel GALC Gene Mutations Causing Krabbe Disease" Human Mutation, 2010, pp. E1894-E1914, vol. 31.
Wenger, David A. et al., "Krabbe Disease: Genetic Aspects and Progress toward Therapy" Molecular Genetics and Metabolism, 2000, pp. 1-9, vol. 70.
International Search Report for PCT/DK2013/050260 dated Oct. 28, 2013.

* cited by examiner

*Primary Examiner* — Titilayo Moloye
(74) *Attorney, Agent, or Firm* — Knobbe Martens Olson & Bear LLP

(57) ABSTRACT

The present invention relates to an animal model for infantile globoid cell leucodystrophy, and use of said animal model for screening and/or validation of agents which may be useful as a medicament for treatment of globoid cell leukodystrophy.

8 Claims, 6 Drawing Sheets

A

B

A

SEQUENCE LISTING

```
<160> NUMBER OF SEQ ID NOS: 31

<210> SEQ ID NO 1
<211> LENGTH: 2010
<212> TYPE: DNA
<213> ORGANISM: Homo sapiens

<400> SEQUENCE: 1
atggctgcgg ccgcgggttc ggcgggccgc gccgcggtgc ccttgctgct gtgtgcgctg    60
ctggcgcccg gcggcgcgta cgtgctcgac gactccgacg ggctgggccg ggagttcgac   120
ggcatcggcg cggtcagcgg cggcggggca acctcccgac ttctagtaaa ttacccagag   180
ccctatcgtt ctcagatatt ggattatctc tttaagccga attttggtgc ctctttgcat   240
attttaaaag tggaaatagg tggtgatggg cagacaacag acggcactga gccctcccac   300
atgcattatg cactagatga gaattatttc cgaggatacg agtggtggtt gatgaaagaa   360
gctaagaaga ggaatcccaa tattacactc attgggttgc catggtcatt ccctggatgg   420
ctgggaaaag gtttcgactg gccttatgtc aatcttcagc tgactgccta ttatgtcgtg   480
acctggattg tgggcgccaa gcgttaccat gatttggaca ttgattatat ggaatttgg    540 aatgagaggt catataatgc caattatatt aagatattaa gaaaaatgct gaattatcaa   600
ggtctccagc gagtgaaaat catagcaagt gataatctct gggagtccat ctctgcatcc   660
atgctccttg atgccgaact cttcaaggtg gttgatgtta taggggctca ttatcctgga   720
acccattcag caaaagatgc aaagttgact gggaagaagc tttggtcttc tgaagacttt   780
agcactttaa atagtgacat gggtgcaggc tgctggggtc gcattttaaa tcagaattat   840
atcaatggct atatgacttc cacaatcgca tggaatttag tggctagtta ctatgaacag   900 ttgcctatg ggagatgcgg gttgatgacg gcccaagagc catggagtgg gcactacgtg   960
gtagaatctc ctgtctgggt atcagctcat accactcagt ttactcaacc tggctggtat  1020
tacctgaaga cagttggcca tttagagaaa ggaggaagct acgtagctct gactgatggc  1080
ttagggaacc tcaccatcat cattgaaacc atgagtcata acattctaa gtgcatacgg   1140 ccattctttc cttatttcaa tgtgtcacaa caatttgcca cctttgttct taagggatct  1200
tttagtgaaa taccagagct acaggtatgg tataccaaac ttggaaaaac atccgaaaga  1260 tttctttta agcagctgga ttctctatgg ctccttgaca gcgatggcag tttcacactg  1320
agcctgcatg aagatgagct gttcacactc accactctca ccactggtcg caaaggcagc  1380
tacccgcttc ctccaaaatc ccagcccttc ccaagtacct ataaggatga tttcaatgtt  1440 gattaccat tttttagtga agctccaaac tttgctgatc aaactggtgt atttgaatat  1500
tttacaaata ttgaagaccc tggcgagcat cacttcacgc tacgccaagt tctcaaccag  1560
agacccatta cgtgggctgc cgatgcatcc aacacaatca gtattatagg agactacaac  1620
tggaccaatc tgactataaa gtgtgatgtt tacatagaga cccctgacac aggaggtgtg  1680
ttcattgcag gaagagtaaa taaggtggt attttgatta gaagtgccag aggaattttc  1740
ttctggattt ttgcaaatgg atcttacagg gttacaggtg atttagctgg atggattata  1800
```

-continued

```
tatgctttag gacgtgttga agttacagca aaaaaatggt atacactcac gttaactatt    1860
aagggtcatt tcgcctctgg catgctgaat gacaagtctc tgtggacaga catccctgtg    1920
aattttccaa agaatggctg gctgcaatt ggaactcact cctttgaatt tgcacagttt    1980 gacaacttc ttgtggaagc cacacgctaa                                      2010
```

<210> SEQ ID NO 2
<211> LENGTH: 669
<212> TYPE: PRT
<213> ORGANISM: Homo Sapiens

<400> SEQUENCE: 2

```
Met Ala Ala Ala Gly Ser Ala Gly Arg Ala Val Pro Leu Leu
1               5                   10                  15

Leu Cys Ala Leu Leu Ala Pro Gly Gly Ala Tyr Val Leu Asp Asp Ser
            20                  25                  30

Asp Gly Leu Gly Arg Glu Phe Asp Gly Ile Gly Ala Val Ser Gly Gly
            35                  40                  45

Gly Ala Thr Ser Arg Leu Leu Val Asn Tyr Pro Glu Pro Tyr Arg Ser
    50                  55                  60

Gln Ile Leu Asp Tyr Leu Phe Lys Pro Asn Phe Gly Ala Ser Leu His
65                  70                  75                  80

Ile Leu Lys Val Glu Ile Gly Gly Asp Gly Gln Thr Thr Asp Gly Thr
                85                  90                  95

Glu Pro Ser His Met His Tyr Ala Leu Asp Glu Asn Tyr Phe Arg Gly
            100                 105                 110

Tyr Glu Trp Trp Leu Met Lys Glu Ala Lys Lys Arg Asn Pro Asn Ile
            115                 120                 125

Thr Leu Ile Gly Leu Pro Trp Ser Phe Pro Gly Trp Leu Gly Lys Gly
        130                 135                 140

Phe Asp Trp Pro Tyr Val Asn Leu Gln Leu Thr Ala Tyr Tyr Val Val
145                 150                 155                 160

Thr Trp Ile Val Gly Ala Lys Arg Tyr His Asp Leu Asp Ile Asp Tyr
                165                 170                 175

Ile Gly Ile Trp Asn Glu Arg Ser Tyr Asn Ala Asn Tyr Ile Lys Ile
            180                 185                 190

Leu Arg Lys Met Leu Asn Tyr Gln Gly Leu Gln Arg Val Lys Ile Ile
            195                 200                 205

Ala Ser Asp Asn Leu Trp Glu Ser Ile Ser Ala Ser Met Leu Leu Asp
    210                 215                 220

Ala Glu Leu Phe Lys Val Asp Val Ile Gly Ala His Tyr Pro Gly
225                 230                 235                 240

Thr His Ser Ala Lys Asp Ala Lys Leu Thr Gly Lys Lys Leu Trp Ser
                245                 250                 255

Ser Glu Asp Phe Ser Thr Leu Asn Ser Asp Met Gly Ala Asp Cys Trp
            260                 265                 270

Gly Arg Ile Leu Asn Gln Asn Tyr Ile Asn Gly Tyr Met Thr Ser Thr
            275                 280                 285

Ile Ala Trp Asn Leu Val Ala Ser Tyr Tyr Glu Gln Leu Pro Tyr Gly
    290                 295                 300

Arg Cys Gly Leu Met Thr Ala Gln Glu Pro Trp Ser Gly His Tyr Val
305                 310                 315                 320

Val Glu Ser Pro Val Trp Val Ser Ala His Thr Thr Gln Phe Thr Gln
                325                 330                 335
```

Pro Gly Trp Tyr Tyr Leu Lys Thr Val Gly His Leu Glu Lys Gly Gly
                340                 345                 350

Ser Tyr Val Ala Leu Thr Asp Gly Leu Gly Asn Leu Thr Ile Ile Ile
            355                 360                 365

Glu Thr Met Ser His Lys His Ser Lys Cys Ile Arg Pro Phe Leu Pro
        370                 375                 380

Tyr Phe Asn Val Ser Gln Gln Phe Ala Thr Phe Val Leu Lys Gly Ser
385                 390                 395                 400

Phe Ser Glu Ile Pro Glu Leu Gln Val Trp Tyr Thr Lys Leu Gly Lys
                405                 410                 415

Thr Ser Glu Arg Phe Leu Phe Lys Gln Leu Asp Ser Leu Trp Leu Leu
            420                 425                 430

Asp Ser Asp Gly Ser Phe Thr Leu Ser Leu His Glu Asp Glu Leu Phe
        435                 440                 445

Thr Leu Thr Thr Leu Thr Thr Gly Arg Lys Gly Ser Tyr Pro Leu Pro
    450                 455                 460

Pro Lys Ser Gln Pro Phe Pro Ser Thr Tyr Lys Asp Asp Phe Asn Val
465                 470                 475                 480

Asp Tyr Pro Phe Phe Ser Glu Ala Pro Asn Phe Ala Asp Gln Thr Gly
                485                 490                 495

Val Phe Glu Tyr Phe Thr Asn Ile Glu Asp Pro Gly Glu His His Phe
            500                 505                 510

Thr Leu Arg Gln Val Leu Asn Gln Arg Pro Ile Thr Trp Ala Ala Asp
        515                 520                 525

Ala Ser Asn Thr Ile Ser Ile Ile Gly Asp Tyr Asn Trp Thr Asn Leu
    530                 535                 540

Thr Thr Lys Cys Asp Val Tyr Ile Glu Thr Pro Asp Thr Gly Gly Val
545                 550                 555                 560

Phe Ile Ala Gly Arg Val Asn Lys Gly Ile Leu Ile Arg Ser Ala
                565                 570                 575

Arg Gly Ile Phe Phe Trp Ile Phe Ala Asn Gly Ser Tyr Arg Val Thr
            580                 585                 590

Gly Asp Leu Ala Gly Trp Ile Ile Tyr Ala Leu Gly Arg Val Glu Val
        595                 600                 605

Thr Ala Lys Lys Trp Tyr Thr Leu Thr Leu Thr Ile Lys Gly His Phe
    610                 615                 620

Ala Ser Gly Met Leu Asn Asp Lys Ser Leu Trp Thr Asp Ile Pro Val
625                 630                 635                 640

Asn Phe Pro Lys Asn Gly Trp Ala Ala Ile Gly Thr His Ser Phe Glu
                645                 650                 655

Phe Ala Gln Phe Asp Asn Phe Leu Val Glu Ala Thr Arg
            660                 665

<210> SEQ ID NO 3
<211> LENGTH: 643
<212> TYPE: PRT
<213> ORGANISM: homo sapiens

<400> SEQUENCE: 3

Tyr Val Leu Asp Asp Ser Asp Gly Leu Gly Arg Glu Phe Asp Gly Ile
1               5                   10                  15

Gly Ala Val Ser Gly Gly Gly Ala Thr Ser Arg Leu Leu Val Asn Tyr
            20                  25                  30

Pro Glu Pro Tyr Arg Ser Gln Ile Leu Asp Tyr Leu Phe Lys Pro Asn
        35                  40                  45

-continued

```
Phe Gly Ala Ser Leu His Ile Leu Lys Val Glu Ile Gly Gly Asp Gly
    50                  55                  60
Gln Thr Thr Asp Gly Thr Glu Pro Ser His Met His Tyr Ala Leu Asp
 65                  70                  75                  80
Glu Asn Tyr Phe Arg Gly Tyr Glu Trp Trp Leu Met Lys Glu Ala Lys
                 85                  90                  95
Lys Arg Asn Pro Asn Ile Thr Leu Ile Gly Leu Pro Trp Ser Phe Pro
            100                 105                 110
Gly Trp Leu Gly Lys Gly Phe Asp Trp Pro Tyr Val Asn Leu Gln Leu
        115                 120                 125
Thr Ala Tyr Tyr Val Val Thr Trp Ile Val Gly Ala Lys Arg Tyr His
    130                 135                 140
Asp Leu Asp Ile Asp Tyr Ile Gly Ile Trp Asn Glu Arg Ser Tyr Asn
145                 150                 155                 160
Ala Asn Tyr Ile Lys Ile Leu Arg Lys Met Leu Asn Tyr Gln Gly Leu
                165                 170                 175
Gln Arg Val Lys Ile Ile Ala Ser Asp Asn Leu Trp Glu Ser Ile Ser
            180                 185                 190
Ala Ser Met Leu Leu Asp Ala Glu Leu Phe Lys Val Val Asp Val Ile
        195                 200                 205
Gly Ala His Tyr Pro Gly Thr His Ser Ala Lys Asp Ala Lys Leu Thr
    210                 215                 220
Gly Lys Lys Leu Trp Ser Ser Glu Asp Phe Ser Thr Leu Asn Ser Asp
225                 230                 235                 240
Met Gly Ala Asp Cys Trp Gly Arg Ile Leu Asn Gln Asn Tyr Ile Asn
                245                 250                 255
Gly Tyr Met Thr Ser Thr Ile Ala Trp Asn Leu Val Ala Ser Tyr Tyr
            260                 265                 270
Glu Gln Leu Pro Tyr Gly Arg Cys Gly Leu Met Thr Ala Gln Glu Pro
        275                 280                 285
Trp Ser Gly His Tyr Val Val Glu Ser Pro Val Trp Val Ser Ala His
    290                 295                 300
Thr Thr Gln Phe Thr Gln Pro Gly Trp Tyr Tyr Leu Lys Thr Val Gly
305                 310                 315                 320
His Leu Glu Lys Gly Gly Ser Tyr Val Ala Leu Thr Asp Gly Leu Gly
                325                 330                 335
Asn Leu Thr Ile Ile Ile Glu Thr Met Ser His Lys His Ser Lys Cys
            340                 345                 350
Ile Arg Pro Phe Leu Pro Tyr Phe Asn Val Ser Gln Gln Phe Ala Thr
        355                 360                 365
Phe Val Leu Lys Gly Ser Phe Ser Glu Ile Pro Glu Leu Gln Val Trp
    370                 375                 380
Tyr Thr Lys Leu Gly Lys Thr Ser Glu Arg Phe Leu Phe Lys Gln Leu
385                 390                 395                 400
Asp Ser Leu Trp Leu Leu Asp Ser Asp Gly Ser Phe Thr Leu Ser Leu
                405                 410                 415
His Glu Asp Glu Leu Phe Thr Leu Thr Thr Leu Thr Thr Gly Arg Lys
            420                 425                 430
Gly Ser Tyr Pro Leu Pro Pro Lys Ser Gln Pro Phe Pro Ser Thr Tyr
        435                 440                 445
Lys Asp Asp Phe Asn Val Asp Tyr Pro Phe Phe Ser Glu Ala Pro Asn
    450                 455                 460
```

```
Phe Ala Asp Gln Thr Gly Val Phe Glu Tyr Phe Thr Asn Ile Glu Asp
465                 470                 475                 480

Pro Gly Glu His His Phe Thr Leu Arg Gln Val Leu Asn Gln Arg Pro
                485                 490                 495

Ile Thr Trp Ala Ala Asp Ala Ser Asn Thr Ile Ser Ile Gly Asp
            500                 505                 510

Tyr Asn Trp Thr Asn Leu Thr Thr Lys Cys Asp Val Tyr Ile Glu Thr
            515                 520                 525

Pro Asp Thr Gly Gly Val Phe Ile Ala Gly Arg Val Asn Lys Gly Gly
    530                 535                 540

Ile Leu Ile Arg Ser Ala Arg Gly Ile Phe Phe Trp Ile Phe Ala Asn
545                 550                 555                 560

Gly Ser Tyr Arg Val Thr Gly Asp Leu Ala Gly Trp Ile Ile Tyr Ala
                565                 570                 575

Leu Gly Arg Val Glu Val Thr Ala Lys Lys Trp Tyr Thr Leu Thr Leu
                580                 585                 590

Thr Ile Lys Gly His Phe Ala Ser Gly Met Leu Asn Asp Lys Ser Leu
                595                 600                 605

Trp Thr Asp Ile Pro Val Asn Phe Pro Lys Asn Gly Trp Ala Ala Ile
610                 615                 620

Gly Thr His Ser Phe Glu Phe Ala Gln Phe Asp Asn Phe Leu Val Glu
625                 630                 635                 640

Ala Thr Arg

<210> SEQ ID NO 4
<211> LENGTH: 669
<212> TYPE: PRT
<213> ORGANISM: Homo sapiens

<400> SEQUENCE: 4

Met Ala Ala Ala Gly Ser Ala Gly Arg Ala Ala Val Pro Leu Leu
1               5                   10                  15

Leu Cys Ala Leu Leu Ala Pro Gly Gly Ala Tyr Val Leu Asp Asp Ser
            20                  25                  30

Asp Gly Leu Gly Arg Glu Phe Asp Gly Ile Gly Ala Val Ser Gly Gly
            35                  40                  45

Gly Ala Thr Ser Arg Leu Leu Val Asn Tyr Pro Glu Pro Tyr Arg Ser
    50                  55                  60

Gln Ile Leu Asp Tyr Leu Phe Lys Pro Asn Phe Gly Ala Ser Leu His
65              70                  75                  80

Ile Leu Lys Val Glu Ile Gly Gly Asp Gly Gln Thr Thr Asp Gly Thr
                85                  90                  95

Glu Pro Ser His Met His Tyr Ala Leu Asp Glu Asn Tyr Phe Arg Gly
            100                 105                 110

Tyr Glu Trp Trp Leu Met Lys Glu Ala Lys Lys Arg Asn Pro Asn Ile
        115                 120                 125

Thr Leu Ile Gly Leu Pro Trp Ser Phe Pro Gly Trp Leu Gly Lys Gly
    130                 135                 140

Phe Asp Trp Pro Tyr Val Asn Leu Gln Leu Thr Ala Tyr Tyr Val Val
145                 150                 155                 160

Thr Trp Ile Val Gly Ala Lys Arg Tyr His Asp Leu Asp Ile Asp Tyr
                165                 170                 175

Ile Gly Ile Trp Asn Glu Arg Ser Tyr Asn Ala Asn Tyr Ile Lys Ile
            180                 185                 190
```

```
Leu Arg Lys Met Leu Asn Tyr Gln Gly Leu Gln Arg Val Lys Ile Ile
            195                 200                 205

Ala Ser Asp Asn Leu Trp Glu Ser Ile Ser Ala Ser Met Leu Leu Asp
210                 215                 220

Ala Glu Leu Phe Lys Val Val Asp Val Ile Gly Ala His Tyr Pro Gly
225                 230                 235                 240

Thr His Ser Ala Lys Asp Ala Lys Leu Thr Gly Lys Lys Leu Trp Ser
                245                 250                 255

Ser Glu Asp Phe Ser Thr Leu Asn Ser Asp Met Gly Ala Gly Cys Trp
            260                 265                 270

Gly Arg Ile Leu Asn Gln Asn Tyr Ile Asn Gly Tyr Met Thr Ser Thr
        275                 280                 285

Ile Ala Trp Asn Leu Val Ala Ser Tyr Tyr Glu Gln Leu Pro Tyr Gly
    290                 295                 300

Arg Cys Gly Leu Met Thr Ala Gln Glu Pro Trp Ser Gly His Tyr Val
305                 310                 315                 320

Val Glu Ser Pro Val Trp Val Ser Ala His Thr Thr Gln Phe Thr Gln
                325                 330                 335

Pro Gly Trp Tyr Tyr Leu Lys Thr Val Gly His Leu Glu Lys Gly Gly
            340                 345                 350

Ser Tyr Val Ala Leu Thr Asp Gly Leu Gly Asn Leu Thr Ile Ile Ile
        355                 360                 365

Glu Thr Met Ser His Lys His Ser Lys Cys Ile Arg Pro Phe Leu Pro
    370                 375                 380

Tyr Phe Asn Val Ser Gln Gln Phe Ala Thr Phe Val Leu Lys Gly Ser
385                 390                 395                 400

Phe Ser Glu Ile Pro Glu Leu Gln Val Trp Tyr Thr Lys Leu Gly Lys
                405                 410                 415

Thr Ser Glu Arg Phe Leu Phe Lys Gln Leu Asp Ser Leu Trp Leu Leu
            420                 425                 430

Asp Ser Asp Gly Ser Phe Thr Leu Ser Leu His Glu Asp Glu Leu Phe
        435                 440                 445

Thr Leu Thr Thr Leu Thr Thr Gly Arg Lys Gly Ser Tyr Pro Leu Pro
    450                 455                 460

Pro Lys Ser Gln Pro Phe Pro Ser Thr Tyr Lys Asp Phe Asn Val
465                 470                 475                 480

Asp Tyr Pro Phe Phe Ser Glu Ala Pro Asn Phe Ala Asp Gln Thr Gly
                485                 490                 495

Val Phe Glu Tyr Phe Thr Asn Ile Glu Asp Pro Gly Glu His His Phe
            500                 505                 510

Thr Leu Arg Gln Val Leu Asn Gln Arg Pro Ile Thr Trp Ala Ala Asp
        515                 520                 525

Ala Ser Asn Thr Ile Ser Ile Ile Gly Asp Tyr Asn Trp Thr Asn Leu
    530                 535                 540

Thr Ile Lys Cys Asp Val Tyr Ile Glu Thr Pro Asp Thr Gly Gly Val
545                 550                 555                 560

Phe Ile Ala Gly Arg Val Asn Lys Gly Gly Ile Leu Ile Arg Ser Ala
                565                 570                 575

Arg Gly Ile Phe Phe Trp Ile Phe Ala Asn Gly Ser Tyr Arg Val Thr
            580                 585                 590

Gly Asp Leu Ala Gly Trp Ile Ile Tyr Ala Leu Gly Arg Val Glu Val
        595                 600                 605

Thr Ala Lys Lys Trp Tyr Thr Leu Thr Leu Thr Ile Lys Gly His Phe
```

```
            610                 615                 620
Ala Ser Gly Met Leu Asn Asp Lys Ser Leu Trp Thr Asp Ile Pro Val
625                 630                 635                 640

Asn Phe Pro Lys Asn Gly Trp Ala Ala Ile Gly Thr His Ser Phe Glu
                645                 650                 655

Phe Ala Gln Phe Asp Asn Phe Leu Val Glu Ala Thr Arg
                660                 665

<210> SEQ ID NO 5
<211> LENGTH: 643
<212> TYPE: PRT
<213> ORGANISM: Homo Sapiens

<400> SEQUENCE: 5

Tyr Val Leu Asp Asp Ser Asp Gly Leu Gly Arg Glu Phe Asp Gly Ile
1               5                   10                  15

Gly Ala Val Ser Gly Gly Ala Thr Ser Arg Leu Leu Val Asn Tyr
                20                  25                  30

Pro Glu Pro Tyr Arg Ser Gln Ile Leu Asp Tyr Leu Phe Lys Pro Asn
                35                  40                  45

Phe Gly Ala Ser Leu His Ile Leu Lys Val Glu Ile Gly Gly Asp Gly
50                  55                  60

Gln Thr Thr Asp Gly Thr Glu Pro Ser His Met His Tyr Ala Leu Asp
65                  70                  75                  80

Glu Asn Tyr Phe Arg Gly Tyr Glu Trp Trp Leu Met Lys Glu Ala Lys
                85                  90                  95

Lys Arg Asn Pro Asn Ile Thr Leu Ile Gly Leu Pro Trp Ser Phe Pro
                100                 105                 110

Gly Trp Leu Gly Lys Gly Phe Asp Trp Pro Tyr Val Asn Leu Gln Leu
            115                 120                 125

Thr Ala Tyr Tyr Val Val Thr Trp Ile Val Gly Ala Lys Arg Tyr His
130                 135                 140

Asp Leu Asp Ile Asp Tyr Ile Gly Ile Trp Asn Glu Arg Ser Tyr Asn
145                 150                 155                 160

Ala Asn Tyr Ile Lys Ile Leu Arg Lys Met Leu Asn Tyr Gln Gly Leu
                165                 170                 175

Gln Arg Val Lys Ile Ile Ala Ser Asp Asn Leu Trp Glu Ser Ile Ser
                180                 185                 190

Ala Ser Met Leu Leu Asp Ala Glu Leu Phe Lys Val Val Asp Val Ile
            195                 200                 205

Gly Ala His Tyr Pro Gly Thr His Ser Ala Lys Asp Ala Lys Leu Thr
210                 215                 220

Gly Lys Lys Leu Trp Ser Ser Glu Asp Phe Ser Thr Leu Asn Ser Asp
225                 230                 235                 240

Met Gly Ala Gly Cys Trp Gly Arg Ile Leu Asn Gln Asn Tyr Ile Asn
                245                 250                 255

Gly Tyr Met Thr Ser Thr Ile Ala Trp Asn Leu Val Ala Ser Tyr Tyr
                260                 265                 270

Glu Gln Leu Pro Tyr Gly Arg Cys Gly Leu Met Thr Ala Gln Glu Pro
            275                 280                 285

Trp Ser Gly His Tyr Val Val Glu Ser Pro Val Trp Val Ser Ala His
            290                 295                 300

Thr Thr Gln Phe Thr Gln Pro Gly Trp Tyr Tyr Leu Lys Thr Val Gly
305                 310                 315                 320
```

His Leu Glu Lys Gly Gly Ser Tyr Val Ala Leu Thr Asp Gly Leu Gly
            325                 330                 335

Asn Leu Thr Ile Ile Ile Glu Thr Met Ser His Lys His Ser Lys Cys
        340                 345                 350

Ile Arg Pro Phe Leu Pro Tyr Phe Asn Val Ser Gln Gln Phe Ala Thr
            355                 360                 365

Phe Val Leu Lys Gly Ser Phe Ser Glu Ile Pro Glu Leu Gln Val Trp
        370                 375                 380

Tyr Thr Lys Leu Gly Lys Thr Ser Glu Arg Phe Leu Phe Lys Gln Leu
385                 390                 395                 400

Asp Ser Leu Trp Leu Leu Asp Ser Asp Gly Ser Phe Thr Leu Ser Leu
            405                 410                 415

His Glu Asp Glu Leu Phe Thr Leu Thr Thr Leu Thr Thr Gly Arg Lys
        420                 425                 430

Gly Ser Tyr Pro Leu Pro Pro Lys Ser Gln Pro Phe Pro Ser Thr Tyr
            435                 440                 445

Lys Asp Asp Phe Asn Val Asp Tyr Pro Phe Phe Ser Glu Ala Pro Asn
450                 455                 460

Phe Ala Asp Gln Thr Gly Val Phe Glu Tyr Phe Thr Asn Ile Glu Asp
465                 470                 475                 480

Pro Gly Glu His His Phe Thr Leu Arg Gln Val Leu Asn Gln Arg Pro
            485                 490                 495

Ile Thr Trp Ala Ala Asp Ala Ser Asn Thr Ile Ser Ile Ile Gly Asp
        500                 505                 510

Tyr Asn Trp Thr Asn Leu Thr Ile Lys Cys Asp Val Tyr Ile Glu Thr
            515                 520                 525

Pro Asp Thr Gly Gly Val Phe Ile Ala Gly Arg Val Asn Lys Gly Gly
        530                 535                 540

Ile Leu Ile Arg Ser Ala Arg Gly Ile Phe Phe Trp Ile Phe Ala Asn
545                 550                 555                 560

Gly Ser Tyr Arg Val Thr Gly Asp Leu Ala Gly Trp Ile Ile Tyr Ala
            565                 570                 575

Leu Gly Arg Val Glu Val Thr Ala Lys Lys Trp Tyr Thr Leu Thr Leu
        580                 585                 590

Thr Ile Lys Gly His Phe Ala Ser Gly Met Leu Asn Asp Lys Ser Leu
            595                 600                 605

Trp Thr Asp Ile Pro Val Asn Phe Pro Lys Asn Gly Trp Ala Ala Ile
        610                 615                 620

Gly Thr His Ser Phe Glu Phe Ala Gln Phe Asp Asn Phe Leu Val Glu
625                 630                 635                 640

Ala Thr Arg

<210> SEQ ID NO 6
<211> LENGTH: 179
<212> TYPE: DNA
<213> ORGANISM: Homo sapiens

<400> SEQUENCE: 6
agctcggtac cgggggatcc ttatcagccg ccatggctgc ggccgcgggt tcggcgggcc      60
gcgccgcggt gcccttgctg ctgtgtgcgc tgctggcgcc cggcggcgcg tacgtgctcg     120
acgactccga cgggctgggc cgggagttcg acggcatcgg cgcggtcagc ggcggcggg      179

<210> SEQ ID NO 7
<211> LENGTH: 69

```
<212> TYPE: DNA
<213> ORGANISM: Homo sapiens

<400> SEQUENCE: 7
gcaacctccc gacttctagt aaattaccca gagccctatc gttctcagat attggattat      60
ctctttaag                                                             69

<210> SEQ ID NO 8
<211> LENGTH: 64
<212> TYPE: DNA
<213> ORGANISM: Homo sapiens

<400> SEQUENCE: 8
ccgaattttg gtgcctcttt gcatatttta aaagtggaaa taggtggtga tgggcagaca      60
acag                                                                  64

<210> SEQ ID NO 9
<211> LENGTH: 114
<212> TYPE: DNA
<213> ORGANISM: Homo sapiens

<400> SEQUENCE: 9
acggcactga gccctcccac atgcattatg cactagatga gaattatttc cgaggatacg      60
agtggtggtt gatgaaagaa gctaagaaga ggaatcccaa tattacactc attg           114

<210> SEQ ID NO 10
<211> LENGTH: 140
<212> TYPE: DNA
<213> ORGANISM: Homo sapiens

<400> SEQUENCE: 10
ggttgccatg gtcattccct ggatggctgg gaaaaggttt cgactggcct tatgtcaatc      60
ttcagctgac tgcctattat gtcgtgacct ggattgtggg cgccaagcgt taccatgatt     120
tggacattga ttatattgga                                                 140

<210> SEQ ID NO 11
<211> LENGTH: 39
<212> TYPE: DNA
<213> ORGANISM: Homo sapiens

<400> SEQUENCE: 11
atttggaatg agaggtcata taatgccaat tatattaag                             39

<210> SEQ ID NO 12
<211> LENGTH: 131
<212> TYPE: DNA
<213> ORGANISM: Homo sapiens

<400> SEQUENCE: 12
atattaagaa aaatgctgaa ttatcaaggt ctccagcgag tgaaaatcat agcaagtgat      60
aatctctggg agtccatctc tgcatccatg ctccttgatg ccgaactctt caaggtggtt     120
gatgttatag g                                                          131

<210> SEQ ID NO 13
<211> LENGTH: 156
<212> TYPE: DNA
<213> ORGANISM: Homo sapiens

<400> SEQUENCE: 13
```

| | |
|---|---|
| ggctcattat cctggaaccc attcagcaaa agatgcaaag ttgactggga agaagctttg | 60 |
| gtcttctgaa gactttagca ctttaaatag tgacatgggt gcaggctgct ggggtcgcat | 120 |
| tttaaatcag aattatatca atggctatat gacttc | 156 |

```
<210> SEQ ID NO 14
<211> LENGTH: 125
<212> TYPE: DNA
<213> ORGANISM: Homo sapiens

<400> SEQUENCE: 14
```

| | |
|---|---|
| cacaatcgca tggaatttag tggctagtta ctatgaacag ttgccttatg ggagatgcgg | 60 |
| gttgatgacg gcccaggagc catggagtgg gcactacgtg gtagaatctc ctgtctgggt | 120 |
| atcag | 125 |

```
<210> SEQ ID NO 15
<211> LENGTH: 128
<212> TYPE: DNA
<213> ORGANISM: Homo sapiens

<400> SEQUENCE: 15
```

| | |
|---|---|
| ctcataccac tcagtttact caacctggct ggtattacct gaagacagtt ggccatttag | 60 |
| agaaaggagg aagctacgta gctctgactg atggcttagg gaacctcacc atcatcattg | 120 |
| aaaccatg | 128 |

```
<210> SEQ ID NO 16
<211> LENGTH: 90
<212> TYPE: DNA
<213> ORGANISM: Homo sapiens

<400> SEQUENCE: 16
```

| | |
|---|---|
| agtcataaac attctaagtg catacggcca tttcttcctt atttcaatgt gtcacaacaa | 60 |
| tttgccacct ttgttcttaa gggatctttt | 90 |

```
<210> SEQ ID NO 17
<211> LENGTH: 87
<212> TYPE: DNA
<213> ORGANISM: Homo sapiens

<400> SEQUENCE: 17
```

| | |
|---|---|
| agtgaaatac cagagctaca ggtatggtat accaaacttg gaaaaacatc cgaaagattt | 60 |
| cttttaagc agctggattc tctatgg | 87 |

```
<210> SEQ ID NO 18
<211> LENGTH: 151
<212> TYPE: DNA
<213> ORGANISM: Homo sapiens

<400> SEQUENCE: 18
```

| | |
|---|---|
| ctccttgaca gcgatggcag tttcacactg agcctgcatg aagatgagct gttcacactc | 60 |
| accactctca ccactggtcg caaaggcagc tacccgcttc ctccaaaatc ccagcccttc | 120 |
| ccaagtacct ataaggatga tttcaatgtt g | 151 |

```
<210> SEQ ID NO 19
<211> LENGTH: 181
<212> TYPE: DNA
<213> ORGANISM: Homo sapiens

<400> SEQUENCE: 19
```

```
attacccatt ttttagtgaa gctccaaact ttgctgatca aactggtgta tttgaatatt    60
ttacaaatat tgaagaccct ggcgagcatc acttcacgct acgccaagtt ctcaaccaga   120
gacccattac atgggctgcc gatgcatcca acacaatcag tattatagga gactacaact   180
g                                                                  181

<210> SEQ ID NO 20
<211> LENGTH: 164
<212> TYPE: DNA
<213> ORGANISM: Homo sapiens

<400> SEQUENCE: 20
gaccaatctg actataaagt gtgatgtata catagagacc cctgacacag gaggtgtgtt    60
cattgcagga agagtaaata aaggtggtat tttgattaga agtgccagag gaattttctt   120
ctggattttt gcaaatggat cttacagggt tacaggtgat ttag                   164

<210> SEQ ID NO 21
<211> LENGTH: 77
<212> TYPE: DNA
<213> ORGANISM: Homo sapiens

<400> SEQUENCE: 21
ctggatggat tatatatgct ttaggacgtg ttgaagttac agcaaaaaaa tggtatacac    60
tcacgttaac tattaag                                                  77

<210> SEQ ID NO 22
<211> LENGTH: 181
<212> TYPE: DNA
<213> ORGANISM: Homo sapiens

<400> SEQUENCE: 22
ggtcatttca cctctggcat gctgaatgac aagtctctgt ggacagacat ccctgtgaat    60
tttccaaaga atgctgggc tgcaattgga actcactcct ttgaatttgc acagtttgac    120
aactttcttg tggaagccac acgctaatac ttaacgggg ccggaattca cgcgtggtac   180
c                                                                  181

<210> SEQ ID NO 23
<211> LENGTH: 16922
<212> TYPE: DNA
<213> ORGANISM: Artificial sequence
<220> FEATURE:
<223> OTHER INFORMATION: rhGALC targeting vector
<220> FEATURE:
<221> NAME/KEY: misc_feature
<222> LOCATION: (16899)..(16906)
<223> OTHER INFORMATION: n is a, c, g, or t

<400> SEQUENCE: 23
ttcagatatc actagtccct gtttctggag ggatgcttct cttgactgag gaggctggca    60
aatctgcttg tatcaagaag agaaaccagc agtgttgtgg ggacaggaaa ttgcgctcgt   120
attttgtcat aagccaatga ggaagcagcc ttttaatgag aaggcttact ttgtctgagt   180
tcaaggatcc ttctgtactt ttaagcgatg tttgggtcat ttactgtcat gtgattttca   240
taacccattc ttttgtatc ttaattataa atgaatactt atatgtatgc ctatttcatg   300
catatgtatg tgtctgatgt atgcacacat gtgtatgcag ctgtgtcacc agtatgcact   360
cttttggaaa ccaggaacct gtcctgtttg cctttctctg ccttatgcct ctgcacaggg   420
```

```
cctcttactg atcctggaac tggactggtg gctagcaagc tccagtgatc ttcctgtctc    480
agcttgtcca ctgtgttggg gctctcagca tccgcattag ttatgcatag cttttaactt    540
gagcactagg atctcagccc aggtcctcat actgtgcagc aagcactctt ccccagattt    600
tcatctctac accctctgaa tttgatgctg ttcttaacat tgcaaccatt caatccttta    660
catcatcttc atcctgttcc tgcatctgcc gttagattga ctgtgcaggc atctacacag    720
gtcctgacta ttccgtggaa atgagcatag ccccatgtaa gagagggcta tattcgctga    780
caccctggat gccccagaag cagaggtaga cggttctaga tgctcatgaa tgagacagga    840
tgagtaatct gggtgtgagg atggagaggc tactgtggac cactgtgggg tgagctggtt    900
catgaagaat aaagcagaag aggcagaatg ggattggtga ttactgtggt ttaacagcaa    960
aactaggcgg ggatgtgagt aggtcaagag agccaacttt gggagaactt ttttctgttc   1020
ttctggggaa ctaatacgat tggatgtata gtatttgatt acagaatcac tttctcttct   1080
agtaatcctc tgggaataga aaacagtgat tcctaaaagc agctgatggg actggaccag   1140
acaaatagat aatcatgcaa tgtgaaaatg tgtttatgag tgctatagat tattatttta   1200
aaacgctaat gcagtacttt aacaaagtaa aactataagt agttaaatca aagtgaaatt   1260
agtttctaga acatcccact tttgagaaaa gttagacata atttttaaac tgtattccaa   1320
taaactttga ttagaaatta aggctaggat attatttat  aagtacgaaa tcaattgaga   1380
gtggaaaatt ctaacttaat tttaggctct actcaggata tgccaagtct gtgtttgtag   1440
atggaaaaaa aaagtgctct tatgatatac ttgagacatt tcttcccgca gttaactgtg   1500
gtatagaaga ggaatgtaaa ggcttttgaa aattccttag tatatcttta tgaatcataa   1560
aaatatgccg gctgtggtgg cacacatctt taatcccagc atctgggagg caggggcaga   1620
tggatctctg agttcaaggc tagcctggtc tatccagtga gttccaggat agatagagta   1680
cactctggct caaaaacaag caagcaagca agcaagcaag caagcaaaga aacaaacaaa   1740
caagcagtaa cgaaaaaaaa gaatgataaa aataatgaat tgtgaagta  ttcaagaatt   1800 tgtaaataac aagtagtaac tgaaaatctc aggatatatt gtcattggga tgatggaaaa   1860
ttaaggtaaa atgtacaaac aataatgacc tgaggcgtta gggcttgggg gtgggggtc    1920 cgcttaatac agggtttccc ttgcaaccat ggagattcga gttcgagctt caggagcaag   1980
gtccaaacag tcacgtgtgg tggcatatga tcatgatcct aggcctggga aggcagaggc   2040
aggcaaactc tgggttaaag aaagacttgt ctttagttta gaagaaagaa caaagagaa    2100 tggtgaagcc tgaggaacaa gtcccaaggt ggccctcagg ctggcacaca catctgcaca   2160
catcactcac atacatacat acagaaacaa gggaattaaa aatttgccaa aatgaaaata   2220
ataatttctg tctgctcatg acgacaatcc ccatgtctct ttttttgcttg gttttgcaca   2280 tttgtctaac tgttgtttct atttcatggg tagttcacga tttgcacaat atctaatttt   2340
acctagatag accatacttc tcttttttaga gaaagagtat tttcacatcc atattaaata   2400
tctatgcact ttactcttca aacactggag gaaaaaaaaa aagaggatg  tagttagaga   2460 acatgagaaa tacaaacttt gacttctgct tacagaagaa aaaaatgtta gtgagcaaaa   2520
attgcttcct tcacacaagg agacactgac ttttgtggat tctgcatctt gtttagttaa   2580
aactgcactg gtgccatatt taacccagtg gcatttaaat gaatagttgg cgaaatttca   2640
gagcccagag acacggaggc attttgacaa tataaaggcc aaatcaataa acaattattc   2700
agaacattgg ctttatgggg tcaggattct ttgccagtca gttttctgat cttctgagat   2760
cacagtgggc acccaacact ggccagaggc agcgcacttg ggcttaaaac gggaaacggg   2820
```

```
gcaaatgaat gtggtccgtc tggattacag cttctccatg cggtagacag cgtggtagtt    2880
attctgctga tgaaggacat tttcctcctt tctccttttt aagctgcatc acttgtctgg    2940
tgcaatttcc gagattaaaa acagcggtca aatagggcaa ggtcaagttc tgacaccctg    3000
gtatgcattc tcatttttat ttctctttat acatttaatt agtcatgttg tatttgtggc    3060
ctgatgaaaa agggttcttg gcagaaagtg agagtggaac aggctatggg tttagttttg    3120
aaagaggtga ccatgagcaa tgggaaggct ggggttctgg gctccgtgct tggggaaatc    3180
ctgttgacat ccaaattttg ataagaaa ttcataaagg aagggctttt agaaaattaa    3240
gtatgaagac aataatatag tttttttatta attaaatatg gcgaaggtaa tatctggggt    3300
taagtaaaat aaactatcaa ggttaatgtt ctgccttgac attagtatgg ctaatagaaa    3360
gttcgaatgc tctctgtgtt tggtgttctc tctctgtcgg gcagcattgt gctggatgtt    3420
gaaataatcg ttctgttgaa ctgtgttgtg gtttgaacaa gaaacgtttc gcagaacctg    3480
tgtgtgaaca cttggttccc actggcagtg ctgtttgagg aaggttgtag aacccttaag    3540
ggccagtaaa aatgggccct gattttgtca tagtctgtcc ccacttctta tcactgtgtg    3600
tttcctgctt gtggacacaa ggtgaccagg cccatgacac ctgatgccct gttatccctg    3660
ctgtgatgta ttaaacgttg tcttcaacat taggacaaat aaaccctctc tccctcaagt    3720
tgcttcttgc cagttatttg gttacagtga cagaaaacta gaaaacaagg gtaattaaca    3780
taaactgtca ttttcttcag cgctgctagg agctcagtag actctaaaat tcctctcttg    3840
acagttgata ttgacagttg aaaggagact aagcatacgt ccgctgcagc atgggactga    3900
aacctcctgg ctttctatta cttgaacaaa tctttgcagt aaacattact gacaaaggag    3960
ctacaggcag aggaggcagt tttcacagtg gagggattgg ctgtcatgat cacattcgcc    4020
aaggactata ttcagccggc gttctttgct gcaaacaaca gaaactgtag tcacctggcc    4080
caaaaagtga ttgggaaatc ggtcaggata tatatggtcc atgatctatg cagagccctg    4140
aggatgaggc ttagagaaaa tggttagaga tagagaacgg aaaaccaggt caccccacct    4200
agatattcag gttaggatgg cactgctgac cccattgtgc tggccccttg aggacactt    4260 agctggagtc tctgtggcac tcctgggtt ccagtatgat agatccattc tcaaacgtca    4320
ctctttcaag gtcaaagtgc agcttcgagg agctgattga agggtctggt tactgtcaga    4380
gcctgcactg gaagcaagaa gagggaaact ctgctatctt cattctggaa ggcagtcgaa    4440
ttctgcctcc caacacgctt agcactgggc agcagtgata ggcatagatt atcatagaac    4500
caaaactcag agcaaaacaa gggctggata gatgcctcag tgggcaaagg tgaccatcat    4560
caagcttgct gacccaagtt taaaccctgg gagccctgtg gtgggaggga acctctgacc    4620
ccatgtgtgt gcagtgtcct gagtgcgcaa ccccccaaag aaacaaagat ctcataaaag    4680
gagaaaaaag agaaaaagcc ttaaaacaag aacgcaaaaa caaagtgca ctcagtccgc    4740 actctggaat aaatccaaac caatacaaaa gtagaaatct atttttccctg atttgctgag    4800 atgtggggg gggggggga aggtacactc aaaacaccct attgataaat ttgtaaatca    4860
tttatgtagc atgctgtaat gccacgggct gatcactctt ttgagggctg tgtgaatact    4920
aacttgactg aatctcctac tggtgcaatg ctggcatcag tttgtagagg gggatactca    4980
agtccaaagg ggctaagtgc cgtatccata acctataccct gtaggttgg aggagagaga    5040 tttgaggcca agctgtctgg agactaagag ccaacattgt taccacagtt agtcatggct    5100
ttatatgcat gtactcttaa ggaaagcccc gtaaacaatg tacaattcac tgaacatggt    5160
```

-continued

```
ggattctttc ctctgaacca ttttcattgc tatctaagga tatgaggtaa cagaactcta    5220
ttatgtattc aaaatttta ttttatttat atgggtgtat atatgtctgg tatactttgt    5280
acacccagtg cccatacagg ccagaagagg gtgacagatc ccttgggatt agggttacag    5340
atggttgtgc tccaccatat gggtactgag aatcgaacct gggtcatctg gaagagttgt    5400
cattgctctt aatccttatc tctgagattc tcattatgtg tgtcatctat ctacctgtct    5460
atctatctgt gtataatttg taaaattata tattaacatt atatataact tatgtgtatg    5520
aatgtttgtg agtgcattca cacatgtgtg agtcatatgt gtaatatatg taatatgttt    5580
atattacaaa tgtttatgtt atgtgcatga atgtgtctgt gtgagtgtgt gcacgcatat    5640
ttgtctgcat gtttgtagat agaggcagga cagccagact agggtgttgg ctgactaggt    5700
acaggaggag ttaaaggtgt ttgctgatgc cagacttgga aagtactggg atccagactc    5760
tagtgctccc acctctgcat gtagtgctct taaccctgag ccatctcacc agccccataa    5820
tcacagattc tttggatgga cgttcattta aagttgctg tcagaaacaa cggcaatcag    5880
acaactcgat ccagagttga aagctcagat gtacaagcag atattacagg atgtctgtaa    5940
agagataagc tttcatatcc ttttacactc tggggatacc tacctcaaag gaatgtttcc    6000
aacactttta gtgagtaatt gtttcatctt atctcctcat gtgaccagtg acttttttta    6060
cgttcaagaa ttatacacta actacgtgta tgagttggac actgcttaga acatgcatgt    6120
acatatacac tgtgatagaa cagatatgat gggctggtat gaaccttaat cagcactttt    6180
gcttaaaagg caagattgct catctttctc aaggttgatt tctctcttaa cttacagaaa    6240
ggagaagttt tgaggaacat aaataggcta ctcagaaaca cttctaattt aaaatggttt    6300
aaaagaacac atttgaaaca tgagacctgg gaccttcctc ttctagtctt atgtcatcga    6360
tcctgaatcc atacatttaa gagaacctat gaacaggatt gcttctctga taactgtgat    6420
ttctcttttt ctcacatact ggtgaatttt cttttccagt ctgcatacat gactttgctt    6480
aacaggaata tttcttgttt gttttccgag tatagatcag aaatcggaaa caagagctgt    6540
gtgctttgat ccatgaactg tagtgcttcc agggtgggta tcatttctgt taatggtttc    6600
tgtatcctat tctgtattgt tcacccattg cacaaaatct gcaaccagtg tgccaattag    6660
aagttggaat ggcatgctac agtatggcat gtgctgtatg ttggcttcaa acttcctgtt    6720
ttcatgagtg tggtatgtgt tccaggtttg atgagagacc ctaactcaaa atagaaggta    6780
aagagagttt gggaaatgac tcagtcgata agaacacact gctcaagcat gggacatata    6840
acaggtggca ggcaactgta atcccagtgc ttcagagggt gaaggagaca gatagattac    6900
tgcaccttgc tgttcagtga gaaatcttgt ctcaagggaa taaggtagaa agtgatagag    6960
acagacaccc gaggacctgc tctggccttt ttgaggactc atgtgcacat ctctaaatat    7020
gtttgaatat aaaacacaca cattcataca catagacaca caaattatgt gaagagtttg    7080
aggaagccac ttgctttgaa ccactggtct acacacacac acacacacac acacacacac    7140
acacgaagaa gaaggaggag gaggagaaag aggaatgaac acaggtatag tattgctcag    7200
aaagacaatg gtttgatttt atcctttcat ataatttccc atatttgtgt ttgtggtggt    7260
taatcttcat tatcaacttg actgaattta gaatcaccac aaaacacacc tctgggcgtg    7320
tctatgaagg tcttccctga aagacttatc tgaagaggga agctgtcata agtcctggat    7380
ggaacaaaaa gaaggaagta aactgaatgc cagcatgttc acctctcttg gatttcctga    7440
ctggagatgc aacaccacca ggtgtctcgg ggtactgctg tcatgactct cctgccaagg    7500
attgcaccct ccaactgtaa gccaagacaa acctttctgt ctttaagttc tttagcacat    7560
```

```
agtacaattg ttacagcacc gagtaaaagt actgaagaca gtagtcttga aacacagatt    7620
taggtttgtc tttaaggggg agcacaactt attccaaaga tagttatgca aagcctatga    7680
tctcttaagc cccagggcct gtcctgtgtc ttctccttgc cactctggtg tctcaggggc    7740
ttgggtggga aactcagctt attgtatgct ttctactaaa gggggagaga gagagagaga    7800
gagagagaga gagagagaga gagagagaga gagattgatt tctacaaaat taggggaatc    7860
taaattctca ggacagttca ctttcctatc acatcagtct tactgacagt ggaaggtagc    7920
ttatgattgt ttcgaggaag cataatttca cctttgtcat ccttgggtcc taagaattaa    7980
actgctgtga cagactagat ggatgaagca cataaattta agttacaggg cacagggcca    8040
taccctaaga aattgaagac tccccccccc aaacaaacaa acaaacaaac agttaatgat    8100
aaacatgctg aatctgatca ggagcaattt aggttgtaaa atgtgccagg cagagaggca    8160
gagaggcaga gaggcaggca gagagacaga gagagaggca gagaggcaga gaggcagaga    8220
ggcaggcaga gaggcagaga ggcagagagg cagaggcaga gaggcagaga ggcagagagg    8280
cagaggcagg cagaactctc tgagttcaag gtgagactgg tagatggaac aagttctaag    8340
aacacaagct gccagcaggc acgtccaacc ttttcttatc ctgacactat gttgtccgct    8400
atagacttca cacttgaggt ctgcacagtt gactatttta atcataaaaa gtcacagaat    8460
gtcttgagtt aagtttatgt acaattttgg ggtagggtgc tttcatagca atcatctgct    8520
ccatgtggtc tcaggcacag gttggatgca cctgccaggg tatttaactg ggtagagaag    8580
tgaataggaa ggcaagggtt actgtaacag gagttggcaa acattaccac ttcctctatg    8640
taagtcaggg catctttcat aagtgatttt catagtcatt ttttattcaa gaaacagaat    8700
aaaggtccga gtattctgaa cctattgtat tttttaggtc tcgcaattca aattactata    8760
tagcaacatt ttggacgagt aatcatatta actcttttaa ggctaaaaga cctggatata    8820
gcagactact caatcgaaca aactttgtca gctagcattt gctaagtgta tataagtgca    8880
caattatgac ttcccgagtg cctattatct tacttttatc ttatccggag ttccctgact    8940
tgctgttctg gtctcacggt ggtttagaaa aattcagggt cctcaagcca agcgactcaa    9000
ccaaggtgac cgcttaactg ggggcgctta aagccaggtc ctcattgctg tttcctactg    9060
ggaatgctcg gctagagtag gaccactcaa agccctcttt tgaccgttgt tgaccattca    9120
cttcccgttt tctaagatga tccatcaggt gaggtaggaa gagtggtcac taagtaatta    9180
cacgcagaga ccggtcccgc ctctttgaca cagaagtgac aaggcaaagc tcgctcaacc    9240 agcccccac cccgcccccc cagctcaaca caacagcggc tgcgcggaca gcccgcagcc    9300
ctcacttaag atggcgaaag cttcctcagc cgcccgctct tcttcctcag ggaggcgatc    9360
gggcccgcct ccccgggcgc cacagtcgcg tgacccgcac aatggctgag tggctactct    9420
cggcttcctg gcaacgccga gcgaaagcta tgactgcggc gcgggttcg gcgggccgcg    9480 ccgcggtgcc cttgctgctg tgtgcgctgc tggcgcccgg cggcgcgtac gtgctcgacg    9540
actccgacgg gctgggccgg gagttcgacg gcatcggcgc ggtcagcggc ggcggggcaa    9600
cctcccgact tctagtaaat tacccagagc cctatcgttc tcagatattg gattatctct    9660
ttaaggtaat gaaaacataa ttatttcatg gtacctgtga tattttagaa attggatggt    9720
gaatttcacc atagaattta ttagcctcac aattctagtt tttgaaaaaa tggcacatta    9780
cttttggaat aaaattgctat ttgaagtttt gcttttgttt ttgcgtctgt aaaacctaag    9840
gcagtaatta gtaattgtct tgaagcttca tacaatacaa cactatgtta atactgttac    9900
```

```
ttcttttcac agccgaattt tggtgcctct ttgcatattt taaaagtgga aataggtggt    9960
gatgggcaga caacagacgg cactgagccc tcccacatgc attatgcact agatgagaat   10020
tatttccgag gatacgagtg gtggttgatg aaagaagcta agaagaggaa tcccaatatt   10080
acactcattg ggttgccatg gtcattccct ggatggctgg gaaaaggttt cgactggcct   10140
tatgtcaatc ttcagctgac tgcctattat gtcgtgacct ggattgtggg cgccaagcgt   10200
taccatgatt tggacattga ttatattgga atttggaatg agaggtcata taatgccaat   10260
tatattaaga tattaagaaa aatgctgaat tatcaaggtc tccagcgagt gaaaatcata   10320
gcaagtgata atctctggga gtccatctct gcatccatgc tccttgatgc cgaactcttc   10380
aaggtggttg atgttatagg ggctcattat cctggaaccc attcagcaaa agatgcaaag   10440
ttgactggga agaagctttg gtcttctgaa gactttagca cttaaaatag tgacatgggt   10500
gcagactgct ggggtcgcat tttaaatcag aattatatca atggctatat gacttccaca   10560
atcgcatgga atttagtggc tagttactat gaacagttgc cttatgggag atgcgggttg   10620
atgacggccc aggagccatg gagtgggcac tacgtggtag aatctcctgt ctgggtatca   10680
gctcatacca ctcagtttac tcaacctggc tggtattacc tgaagacagt tggccattta   10740
gagaaaggag gaagctacgt agctctgact gatggcttag ggaacctcac catcatcatt   10800
gaaaccatga gtcataaaca ttctaagtgc atacggccat tcttccctta tttcaatgtg   10860
tcacaacaat ttgccacctt tgttcttaag ggatctttta gtgaaatacc agagctacag   10920
gtatggtata ccaaacttgg aaaaacatcc gaaagatttc tttttaagca gctggattct   10980
ctatggctcc ttgacagcga tggcagtttc acactgagcc tgcatgaaga tgagctgttc   11040
acactcacca ctctcaccac tggtcgcaaa ggcagctacc cgcttcctcc aaaatcccag   11100
cccttcccaa gtacctataa ggatgatttc aatgttgatt acccattttt tagtgaagct   11160
ccaaactttg ctgatcaaac tggtgtattt gaatatttta caaatattga agaccctggc   11220
gagcatcact tcacgctacg ccaagttctc aaccagagac ccattacgtg ggctgccgat   11280
gcatccaaca caatcagtat tataggagac tacaactgga ccaatctgac tacaaagtgt   11340
gatgtataca tagagacccc tgacacagga ggtgtgttca ttgcaggaag agtaaataaa   11400
ggtggtattt tgattagaag tgccagagga atttttcttct ggattttttgc aaatggatct   11460
tacagggtta caggtgattt agctggatgg attatatatg ctttaggacg tgttgaagtt   11520
acagcaaaaa aatggtatac actcacgtta actattaagg gtcatttcac ctctggcatg   11580
ctgaatgaca agtctctgtg gacagacatc cctgtgaatt ttccaaagaa tggctgggct   11640
gcaattggaa ctcactcctt tgaatttgca cagtttgaca actttcttgt ggaagccaca   11700
cgctaatcca cacggggcgt caagacatga tttggatttt ctattttttga ttttggttca   11760
gggcgaattc tgattttgat ggatctatat atgagccttt gaggctaacg ataatgagga   11820
gtaaataggg gacatggtgc atttttgctg gatcctgtga aaggtttatt tagagccgat   11880
tccagagggg atgcaggtag tctttgacac tctctgtggt agctctcaag gcccacggtt   11940
gttcagtccc atccttcagg ggtgcttggg cgggttctgc ccttgcagcc ttcgcactaa   12000
taccaaggta gctcattcca cattgtttgt aaatgatcgt gcaggcaact ggggccacag   12060
aggagctttt gtgagcctag ccacacgcct cagtcaaggc ttccttagaa gatggtgatg   12120
ctcaagggga aactgatgag cactacagcg agtacttcac tgtgcagtcg tctctccctc   12180
tccctccatc tcccctcccc tcaccatgcc cctcccccc cccccagga tgatactttt   12240
ggagttgtgt gagatgatgg tgggatgatt tgacaattac ctcattaata aactaacact   12300
```

```
gaagccattt ctgcagtaat aaaaaacaac cagattaact gggttgtttg tactttttaa    12360
cgatcttaca tccaactttt agatgttatc acccttataa ccgccttgag cacatttccc    12420
ccatataagc tggtgccgta ggcgaatcta actgcttccc tgttcatttc ttgtgccttt    12480
tgcagtgagt cctcacaagg ggctctgaac gcagcccagc accggtgaat gccttcatct    12540
gtcaatgtgt ggcaggaggg accgccgagg gtttaactag ctcacagatt tggatcatct    12600
cctgatgttt ttggatagat gcacttaata tattcccagg gtttagattt aaatgttgct    12660
aagcatgttt ctcattagta tgatttatgt aacattaatg taactcttag aaacagacca    12720
gttctccatg tgggtaaagt gaactctgga attctttata aggaaaactt actcattgac    12780
ataacgctgc tccatgggaa ttggtagtgc tccagcgagg cagaagtaca gtgaggtctg    12840
tattacttcc gaaaacttga aaccaaggct aaatgattta ctgtttagat tttaaattat    12900
ttttgaaaaa taacatacaa gtgtaattta tatgtcttaa aatattctca ttttaagtgt    12960
ctagtttgtt ttaataattt tgtaaacatt ccctgtaacc cacactccaa tgaagctact    13020
gaatatttgc atcactccag aaagttctct gctatacctg tgcaatccat tccgctcact    13080
cctaatttca agcaacagtg atgtctctgt tgccaaaata ttgtttgttt tgaaagcatg    13140
gaagtgacag gatgcgctgt ggactcttct ggatgtgtgt tttccgtcag cgggatgctg    13200
taagatttgt ccagtgtgta aggttttgcc aaagtggtac actgctcctt atttctgaag    13260
ggagcagcat tgaatggatg caccaccatt ggttttccat ctcctatttt tatgagatga    13320
aaaataaaag tcatcacagc actaacatac aaatctttga gaatttgcat tgttcttct    13380 ggattaatgg gggaggggg agagattact agctctggtg ttaagatttg tttaacttca    13440
taagaaaccg ccagcattcc tcaagatggt cctgcgatgt tacactcgcc tcagcgtgac    13500
gtcgaagttc ctattccgaa gttcctattc tctagaaagt ataggaactt ctgtgtcagt    13560
tagggtgtgg aaagtcccca ggctccccag gcaggcagaa gtatgcaaag catgcatctc    13620
aattagtcag caaccaggtg tggaaagtcc ccaggctccc cagcaggcag aagtatgcaa    13680
agcatgcatc tcaattagtc agcaaccata gtcccgcccc taactccgcc catcccgccc    13740
ctaactccgc ccagttccgc ccattctccg ccccatggct gactaatttt ttttatttat    13800
gcagaggccg aggccgcctc tgcctctgag ctattccaga agtagtgagg aggcttttt    13860 ggaggcctag gcttttgcaa aaagctcccg ggagcttgta tatccatttt cggatctgat    13920
caagagacag gatgaggatc gtttcgcatg attgaacaag atggattgca cgcaggttct    13980
ccggccgctt gggtggagag gctattcggc tatgactggg cacaacagac aatcggctgc    14040
tctgatgccg ccgtgttccg gctgtcagcg caggggcgcc cggttctttt tgtcaagacc    14100
gacctgtccg gtgccctgaa tgaactgcag gacgaggcag cgcggctatc gtggctggcc    14160
acgacgggcg ttccttgcgc agctgtgctc gacgttgtca ctgaagcggg aagggactgg    14220
ctgctattgg gcgaagtgcc ggggcaggat ctcctgtcat ctcaccttgc tcctgccgag    14280
aaagtatcca tcatggctga tgcaatgcgg cggctgcata cgcttgatcc ggctacctgc    14340
ccattcgacc accaagcgaa acatcgcatc gagcgagcac gtactcggat ggaagccggt    14400
cttgtcgatc aggatgatct ggacgaagag catcaggggc tcgcgccagc cgaactgttc    14460
gccaggctca aggcgcgcat gcccgacggc gaggatctcg tcgtgaccca tggcgatgcc    14520
tgcttgccga atatcatggt ggaaaatggc cgcttttctg gattcatcga ctgtggccgg    14580
ctgggtgtgg cggaccgcta tcaggacata gcgttggcta cccgtgatat tgctgaagag    14640
```

```
cttggcggcg aatgggctga ccgcttcctc gtgctttacg gtatcgccgc tcccgattcg    14700
cagcgcatcg ccttctatcg ccttcttgac gagttcttct gagcgggact ctggggttcg    14760
aaatgaccga ccaagcgacg cccaacctgc catcacgaga tttcgattcc accgccgcct    14820
tctatgaaag gttgggcttc ggaatcgttt tccgggacgc cggctggatg atcctccagc    14880
gcggggatct catgctggag ttcttcgccc accccaactt gtttattgca gcttataatg    14940
gttacaaata aagcaatagc atcacaaatt tcacaaataa agcatttttt tcactgcatt    15000
ctagttgtgg tttgtccaaa ctcatcaatg tatcttatga agttcctatt ccgaagttcc    15060
tattctctag aaagtatagg aacttcacgc gttagagcct ctgatgctgt gcaccgtgtc    15120
tggaatagac tgagatttct gcacatacag ttatgtcatc tgtggccacg gtgctttggc    15180
ttccttcctg gcatgtctgc tttggggcga ggtttctgcc tttgtgctgg ctgcaacttt    15240
caggtccatc actgggaagt attaagggtg tttgccctca ctttgttcca tcttagggag    15300
agtgtctttc ctgttagtgt aatatcctag ctgacttctt ttccctcttc cctttcttta    15360
ctatctttag atgccagttt tctgagattt tttaaaaaat ataagtagga attagatttg    15420
ttaaataccc agtttgatga gataattgta tgtttatctg tttatgtata tattttactc    15480
ttatctgtta tgctgtatat tgcattgtct aatgtccaga tattaaacat ctctgcgttc    15540
cttagatatg tcatgctgaa cggggttccc caccctgtct ctacattggc ggatctcagt    15600
tacaagcatt ggaataaggg tatttgcatc tatacccatg tgcagtattg ccctgttttt    15660
aaaaattata tctttgtctg gtttcagcta gagtggtccc ttctaaaatt aactgggaga    15720
tggtctctct tccttgtttt ttttttcccc caatactttg tgagattctt aaatcttaga    15780
attttctcag tcagggtcca gacgaaagac agaagacaga aaccacacca gaaaagcaaa    15840
acaacaacaa caacaacaaa attaaaacaa aaataacaca aaggatgata actagccaga    15900
tgagataaac tactaagaat taaagaatt ctaatggact tcaagaatcc accaggcctg    15960
tcacagactg cctgcaatcc caacacccag gaggctgagc gtgaattaaa ggacacctgt    16020
gctgcacagt gaaacactgc ttcatttcca cccaagcatc agtagagacc agctacgtcc    16080
ttggctgcag tagcctacca agcacacagc agaggccttt ctcacaggct gatgcttggc    16140
tctcccggaa gctggtttaa cttcagccct gaaggtctgc aagtttcctg agctgcatac    16200
tggagctggc aaccaggaaa cctgctttct ggatcggaca caagactgac aaagggccaa    16260
atacttaaaa tctctgacgt gtgtaacacc gacagttcgt aggcacagat caaacttgaa    16320
agggagtaag tttattctgg agcaaaacat gagtgactcg agcccaggaa cacagactta    16380
ggtcatccca aacgcatgct tctctgtggt agcattttca gggaggtctt agagtaacaa    16440
aacaacagaa gccatcaatc aatgtacttt taaagatgaa tcgatagcat tagtagatgg    16500
gtaacagcaa ggggctgggt gcagtttcca gctatgggtc tcagctgatt cttggtttgg    16560
ggtcagtgga agccagggc ctgttcatac aatctcaaaa gggttttatt tgagggtcac    16620
aggatgttaa ggtcatgcag agttgtcaat cagttaaagg gtaaagatag cccaagatag    16680
tttggttcta gacctgaaat attccagctc tgcatagtta cagaaattct aatcagccaa    16740
tcagccttgg agaatctatt acatagatgc tattattctg ggaatcagtt ctaatatctc    16800
ataaaaaatt ctgataactt ctcaagaaaa tctctcttgg gaagtccaca cccatttttg    16860
gtgtgtattc ttatttttccc aagatcttct cagtcgacnn nnnnnntcgc gagatatctt    16920
ca                                                                   16922
```

```
<210> SEQ ID NO 24
<211> LENGTH: 20
<212> TYPE: DNA
<213> ORGANISM: Artificial Sequence
<220> FEATURE:
<223> OTHER INFORMATION: oligonucleotide 2282_45

<400> SEQUENCE: 24
gcatggaagt gacaggatgc                                                   20

<210> SEQ ID NO 25
<211> LENGTH: 21
<212> TYPE: DNA
<213> ORGANISM: Artificial Sequence
<220> FEATURE:
<223> OTHER INFORMATION: oligonucleotide 2282_46

<400> SEQUENCE: 25
aatatcccag atcgcttcag g                                                 21

<210> SEQ ID NO 26
<211> LENGTH: 20
<212> TYPE: DNA
<213> ORGANISM: Artificial Sequence
<220> FEATURE:
<223> OTHER INFORMATION: oligonucleotide 1260_1

<400> SEQUENCE: 26
gagactctgg ctactcatcc                                                   20

<210> SEQ ID NO 27
<211> LENGTH: 21
<212> TYPE: DNA
<213> ORGANISM: Artificial Sequence
<220> FEATURE:
<223> OTHER INFORMATION: oligonucleotide 1260_2

<400> SEQUENCE: 27
ccttcagcaa gagctgggga c                                                 21

<210> SEQ ID NO 28
<211> LENGTH: 20
<212> TYPE: DNA
<213> ORGANISM: Artificial Sequence
<220> FEATURE:
<223> OTHER INFORMATION: oligonucleotide 2283_48

<400> SEQUENCE: 28
cgtctgctgc agtcaagtgg                                                   20

<210> SEQ ID NO 29
<211> LENGTH: 21
<212> TYPE: DNA
<213> ORGANISM: Artificial Sequence
<220> FEATURE:
<223> OTHER INFORMATION: oligonucleotide 2283_46

<400> SEQUENCE: 29
aatatcccag atcgcttcag g                                                 21

<210> SEQ ID NO 30
<211> LENGTH: 19
<212> TYPE: DNA
<213> ORGANISM: Artificial Sequence
<220> FEATURE:
<223> OTHER INFORMATION: oligonucleotide 1307_1
```

```
<400> SEQUENCE: 30
ggcagaagca cgcttatcg                                                 19

<210> SEQ ID NO 31
<211> LENGTH: 21
<212> TYPE: DNA
<213> ORGANISM: Artificial Sequence
<220> FEATURE:
<223> OTHER INFORMATION: oligonucleotide 1307_2

<400> SEQUENCE: 31
gacaagcgtt agtaggcaca t                                              21
```

ANIMAL MODEL OF KRABBE'S DISEASE

CROSS REFERENCE TO RELATED APPLICATIONS

This application is a U.S. National Phase Application of PCT International Application Number PCT/DK2013/050260, filed on Aug. 7, 2013, designating the United States of America and published in the English language, which is an International Application of and claims the benefit of priority to Danish Patent Application No. PA 2012 70467, filed on Aug. 7, 2012. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-PLOUG212-001APC.txt, the date of creation of the ASCII text file is Jan. 27, 2015, and the size of the ASCII text file is 53 KB.

FIELD OF THE INVENTION

The present invention relates to an animal model for infantile globoid cell leucodystrophy, and use of said animal model for screening and/or validation of agents which may be useful as a medicament for treatment of globoid cell leukodystrophy.

BACKGROUND OF THE INVENTION

Infantile globoid cell leucodystrophy (GLD, galactosylceramide lipidosis or Krabbe's disease) is a rare, autosomal recessive hereditary degenerative disorder in the central and peripheral nervous systems. The incidence in the US is estimated to 1:100.000. It is characterised by the presence of globoid cells (cells with multiple nuclei), degeneration of the protective myelin layer of the nerves and loss of cells in the brain. GLD causes severe mental reduction and motoric delay. It is caused by a deficiency in galactocerebroside-β-galactosidase (GALC), which is an essential enzyme in the metabolism of myelin. The disease often affects infants prior to the age of 6 months, but it can also appear during youth or in adults. The symptoms include irritability, fever without any known cause, stiffness in the limbs (hypertony), seizures, problems associated with food intake, vomiting and delayed development of mental and motoric capabilities. Additional symptoms include muscular weakness, spasticity, deafness and blindness.

Currently, there is no curative treatment of GLD. Results from a very small clinical study, including patients with infantile GLD, revealed that children receiving umbilical cord blood stem cells from non-related donors prior to the onset of symptoms, developed with only little neurological invalidity. The results also showed that progression of the disease was stabilized sooner in patients receiving umbilical cord blood as compared to patients receiving bone marrow from adults. It has appeared that bone marrow transplantation has a beneficial effect in patients with mild disease, if performed early in the course of disease. Generally, infantile GLD is lethal prior to the age of 2. Progression of the disease is generally milder in patients with a later onset of the disease.

Exogenous replacement of missing or deficient enzyme (enzyme replacement therapy, ERT) has proven effective in patients with lysosomal storage disorders such as Gaucher disease. Access to an suitable and reliable animal model of GLD will be of outmost importance for the development of enzyme replacement therapy of GLD.

The galactosylceramidase gene (GALC) is about 60 kb in length and consists of 17 exons. Numerous mutations and polymorphisms have been identified in the murine and human GALC gene, causing GLD with different degrees of severity. Table 1 identifies a number of these mutations and polymorphisms, including the very common, so-called 30-kb deletion. This deletion accounts for a major part of the mutant GALC alleles in individuals of European ancestry. This large deletion results in the classic infantile form when in the homozygous state or when heterozygous with another mutation associated with severe disease. Often, however, the observed phenotypic differences in human patients result not only from the particular mutations and polymorphisms, but also from other, yet unknown factors. This makes it almost impossible to predict the effect of each individual mutation if present in a different context.

TABLE 1

(adopted from Tappino et al., 2010):

| Nucleotide (amino acid) substitution | Type of mutation |
|---|---|
| 127G > C (G43R) | Missense |
| 188G > A (R63H) | Missense |
| 3340G > A (E114K) | Missense |
| 512A > T (D117V) | Missense |
| 701T > C (I234T) | Missense |
| 809G > A (G270D) | Missense |
| 836A > C (N279T) | Missense |
| 870C > T (S287F) | Missense |
| 893A > G (Y298C) | Missense |
| 1027_1036delAAGACAGTTG (K343AfsX3) | Frameshift |
| IVS10del30kb | Deletion |
| 1138C > T (R380W) | Missense |
| 1139G > T (R380L) | Missense |
| 1538C > T (T513M) | Missense |
| 1609G > A (G537R) | Missense |
| 1652A > C (Y551S) | Missense |
| 1739delT (F580SfsX16) | Frameshift |
| 1853delT (L618X) | Nonsense |

A natural model of GLD, known as the "twitcher" (twi) mouse, has a mutation of the GALC gene causing complete lack of GALC activity. Various treatments have been attempted on this mouse model, with varying degrees of success. However, the aggressivity of GLD in the twitcher mouse makes this model sub-optimal, since a moderate therapeutic benefit may be superimposed by rapid deterioration. Utility of the "twitcher" mice is further compromised by the fact that the mice typically die at an age of approximately 40 days, the short lifespan resulting in a very small therapeutic window. Moreover, the "twitcher" mouse model has the disadvantage of not being immunotolerant to exogenous, human enzyme. Indeed, the animals may develop a progressive immunological response to repeatedly injected human GALC, which may reduce therapeutic efficacy and/or induce lethal anaphylactic reactions.

Transgenic introduction of human GALC into "twitcher" mice and studies on the transgenic mice have led to the conclusion that low, even undetectable, levels of GALC activity were able to slow the course of GLD in mice. Based on these observations it was predicted that as little as 5% of normal GALC activity would be enough to delay or even prevent symptoms (Gasperi et al., 2004).

Transgenic mice have also been created by homologous recombination, containing a polymorphic change found in humans: The amino acid at codon 168 in murine GALC was changed from histidine to cysteine (R168C). Studies in relation to these mice confirmed that the problem of generating an exact model a human disease by replacing an amino acid in a protein from a mouse or other species is difficult. First of all, transfection studies in COS-1 cells unexpectedly showed that there is little correlation between the effects on GALC activity of particular amino acid substitutions in human GALC and the effects of changing the same amino acids in murine GALC. In particular, while R168C was known to have little effect in humans it had a profound effect on mouse GALC activity. Secondly, the studies also revealed that even though the transgenic mice had considerable, residual expression of GALC, this was able to slow progression of GLD only slightly (Luzi et al., 2002.

Larger animal models of GLD include rhesus monkeys, cats and dogs. However, like the twitcher mice, these natural models of GLD are not immunotolerant to human GALC.

Hence, there is a need for an improved animal model of GLD, which is immunotolerant to human GALC and has a sufficiently slow disease progression and longer lifespan.

OBJECT OF THE INVENTION

It is an object of the present invention to provide an improved animal model of GLD.

In particular, it may be seen as an object of the present invention to provide a animal model of GLD which is suitable for use in screening and validation of agents which are useful as in therapeutic or prophylactic management of globoid cell leukodystrophy

SUMMARY OF THE INVENTION

An ideal animal model of GLD would have a relatively mild phenotype and slow disease progression and be immonotolerant to human GALC.

Thus, the above described object is intended to be obtained in a first aspect of the invention by providing a pluripotent or totipotent non-human mammal cell comprising at least one exogenous nucleic acid construct encoding a galactocerebroside-beta-galactosidase (GALC), wherein the amino acid corresponding to Glycine at position 270 in human GALC is changed to aspartic acid and the amino acid corresponding to isoleucine at position 546 in human GALC is changed to threonine.

The invention further relates to a method of making a genetically modified non-human mammal comprising the steps of
  (a) providing a pluripotent or totipotent non-human mammal cell according to the invention,
  (b) inserting said pluripotent or totipotent non-human mammal cell into isolated blastocytes of said non-human mammal,
  (c) implanting said blastocytes comprising said pluripotent or totipotent non-human mammal in a pseudopregnant female of said non-human mammal,
  (d) identifying germline transmission in offspring of the pregnant female of step (c).

Another aspect of the invention pertains to a galactocerebrosid-beta-galactosidase (GALC) deficient genetically modified non-human mammal comprising at least one exogenous nucleic acid construct encoding galactocerebroside-beta-galactosidase (GALC), wherein the amino acid corresponding to Glycine at position 270 in human GALC is changed to aspartic acid and the amino acid corresponding to isoleucine at position 546 in human GALC is changed to threonine.

Yet another aspect of the invention provides the use of the genetically modified non-human mammal according to the invention for screening or validation of an agent useful as a medicament for treatment of globoid cell leukodystrophy.

Finally, the invention provides a method of validating an agent, comprising the steps of
  (a) providing a genetically modified non-human mammal according to the present invention,
  (b) contacting said non-human mammal with a agent for validation,
  (c) determining whether said non-human mammal is responsive to said agent after said contact.

The first, second, third, fourth and fifth aspects of the present invention may each be combined with any of the other aspects. These and other aspects of the invention will be apparent from and elucidated with reference to the embodiments described hereinafter.

BRIEF DESCRIPTION OF THE FIGURES

The animal model of GLD according to the invention will now be described in more detail with regard to the accompanying figures. The figures illustrate ways of implementing the present invention but should not be construed as being limiting to other possible embodiments falling within the scope of the attached claim set.

DETAILED DESCRIPTION OF THE INVENTION

Detailed Description of Embodiments

Figure 1:
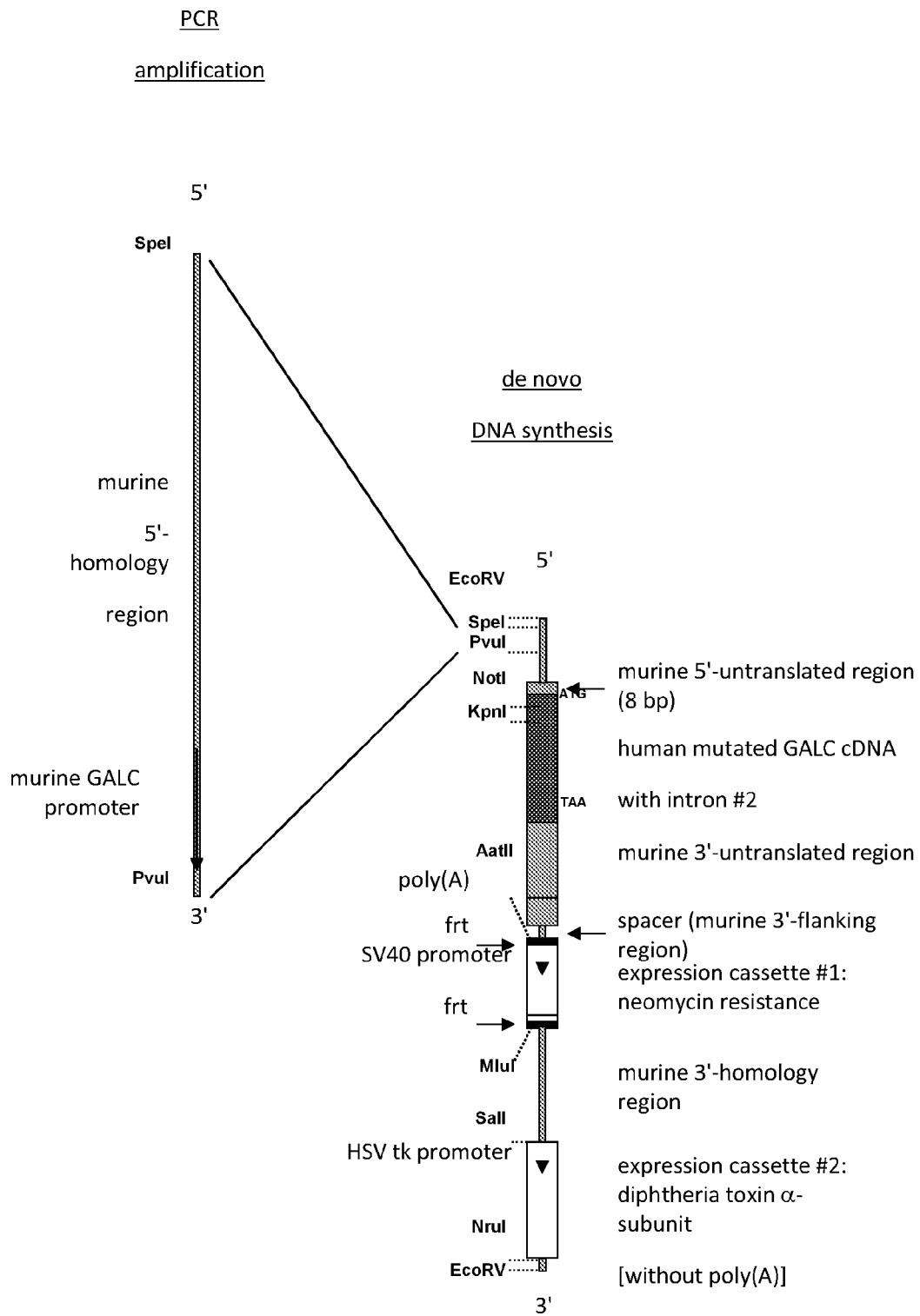
FIG. 1: Design and construction of targeting vector for muring Galc gene knockout/human Galc gene knockin.

The present invention is based on the observation that substitution of glycine at position 270 in the human galactocerebroside-beta-galactosidase with aspartic acid (G270D), is one of the mutations frequently found in GLD patients with a relatively mild phenotype. It is often found together with a polymorphism, where isoleucine at position 546 is changed to threonine (I546T). In addition, the inventors have seen a significant number of patients with the G270D mutation as their one allele and the 30 kb deletion as their second allele. Yet, these patients still have a mild phenotype, indicating that the G270D mutation is definitely a mild mutation in humans and would result in a mild phenotype with slow disease progression, also when present on both alleles.

The present inventors have tested the effect of the G270D mutation and the I546T polymorphism in transfection studies in COS-1 cells. They observed that there was significantly lower GALC activity when the mutation was expressed together with the polymorphism than when expressed with the "normal" background". This was surprising in view of the mild phenotype in the patients, and it led the inventors to hypothesize that human GALC carrying the G270D mutation/I546T polymorphism, if expressed in a suitable animal species such as mice, would reduce the levels of GALC activity sufficiently to induce symptoms of GLD, yet the residual GLAC activity would be sufficient to slow disease progression. In other words, transgenic animals, which are homozygous for the G270D mutation/I546T polymorphism could possibly provide a new approach to development of suitable animal model of GLD. Hence, the present invention is concerned with providing an animal model of GLD in which the animals carry the G270D mutation/I546T polymorphism.

According to a first aspect the present invention provides a pluripotent or totipotent non-human mammal cell comprising at least one exogenous nucleic acid construct encoding a galactocerebroside-beta-galactosidase (GALC), wherein the amino acid corresponding to Glycine at position 270 in human GALC is changed to aspartic acid and the amino acid corresponding to isoleucine at position 546 in human GALC is changed to threonine.

In the present context the phrase "the amino acid corresponding to Glycine at position 270 in human GALC" should be construed so as to define the amino acid residue in a given amino acid sequence, which would be opposite to $Gly_{270}$ in the amino acid sequence of recombinant human wild type GALC as defined in SEQ ID NO: 4, if the two amino acid sequences were aligned to best fit. Likewise, the phrase "the amino acid corresponding to Isoleucine at position 546 in human GALC" should be construed so as to define the amino acid residue in a given amino acid sequence, which would be opposite to $Ile_{546}$ in the amino acid sequence of recombinant human GALC as defined in SEQ ID NO: 4, if the two amino acid sequences were aligned to best fit.

In the context of the present invention, it is preferred that exogenous nucleic acid construct defined above encodes a galactocerebroside-beta-galactosidase, wherein glycine at position 270 (Gly270) is changed to aspartic acid and isoleucine at position 546 (Ile546) is changed to threonine.

It is conceivable that, in addition to the the G270D mutation/I546T polymorphism, it is possible to introduce several other sequence modifications into human galactocerebroside-beta-galactosidase with little or no additional implication on enzymatic activity. SEQ ID NO: 2 provides the sequence of human GALC, including a 26 amino acid leader sequence. The sequence set forth in SEQ ID NO.: 3 is the sequence of mature human GALC, excluding the 26 amino acid leader sequence.

In further embodiments said galactocerebroside-beta-galactosidase thus comprises a sequence, which is essentially identical to the sequence set forth in SEQ ID NO: 3.

The term "essentially identical to" as used in relation to amino acid sequences of the present and any of the following aspects of the invention refers to a polypeptide having a sequence which is at least 95% identical, such as at least 96% identical, at least 97% identical, at least 98% identical, at least 99% identical, at least 99.5% identical or such as at least 99.7% identical, to the sequence set forth in SEQ ID NO: 3. In further embodiments the term "essentially identical to" would imply that this polypeptide has least 80%, preferably at least 85%, more preferably at least 90%, more preferably at least 95%, more preferably at least 95%, more preferably at least 98%, and most preferably at least 99% of the activity of the polypeptide set forth in SEQ ID NO: 3.

For the present purpose "sequence identity" is defined as sequence identity between genes or proteins at the nucleotide or amino acid level, respectively. Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990).

BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

Galactocerebroside-beta-galactosidase belongs to E.C. 3.1.6.46 and is capable of catalysing the reaction of D-galactosyl-N-acylsphingosine+H2O=D-galactose+N-acylsphingosine, thus GALC catalyzes the degradation of galactolipids in for example myelin. The human GALC gene encodes a product of 669 amino acids which includes a 16 amino acids leader or signal sequence. The mature human GALC enzyme is a glycosylated lysosomal enzyme comprising 643 amino acids and having a molecular weight of 72.8 kDa.

Generally, the skilled person will be able to readily devise appropriate assays for the determination of enzymatic activity. However, transfection of COS-1 cells with cDNA encoding the enzyme and subsequent determination of GALC activity in the transfected cells as described herein, is a particular useful assay for that purpose.

In further, particular embodiments the said galactocerebroside-beta-galactosidase comprises or consists essentially of the sequence set forth in SEQ ID NO: 3. Preferably, the said galactocerebroside-beta-galactosidase consists of the sequence set forth in SEQ ID NO: 3.

In equally preferred embodiments, the said exogenous nucleic acid construct comprises a nucleic acid sequence, which is essentially identical to the sequence set forth in SEQ ID NO.: 1. When used in the present context, the term "essentially identical" is to be construed broadly so as to include nucleic acid sequences in which the sequence set forth in SEQ ID NO.: 1 has been modified, such as by insertion, deletion and/or substitution of one or more nucleic acid residues, provided that transcription of the nucleic acid sequence and subsequent translation of the transcription product results in a galactocerebroside-beta-galactosidase which has the amino acid sequence set forth in SEQ ID NO: 2.

TABLE 2

Nucleic acid sequences and amino acid sequences according to the invention.

| Sequence description | Sequence identifier |
|---|---|
| rhGALC c.G809A/c.T1637C coding seq. | SEQ ID NO.: 1 |
| rhGALC G270D/I546T amino acid seq., incl. signal sequence | SEQ ID NO.: 2 |
| rhGALC G270D/I546T amino acid seq., without signal sequence | SEQ ID NO.: 3 |
| rhGALC wt amino acid seq. | SEQ ID NO.: 4 |
| rhGALC wt amino acid seq. without signal seq. | SEQ ID NO.: 5 |
| rhGALC coding sequence, exon 1 | SEQ ID NO.: 6 |
| rhGALC coding sequence, exon 2 | SEQ ID NO.: 7 |
| rhGALC coding sequence, exon 3 | SEQ ID NO.: 8 |
| rhGALC coding sequence, exon 4 | SEQ ID NO.: 9 |
| rhGALC coding sequence, exon 5 | SEQ ID NO.: 10 |
| rhGALC coding sequence, exon 6 | SEQ ID NO.: 11 |
| rhGALC coding sequence, exon 7 | SEQ ID NO.: 12 |
| rhGALC coding sequence, exon 8 | SEQ ID NO.: 13 |
| rhGALC coding sequence, exon 9 | SEQ ID NO.: 14 |
| rhGALC coding sequence, exon 10 | SEQ ID NO.: 15 |
| rhGALC coding sequence, exon 11 | SEQ ID NO.: 16 |
| rhGALC coding sequence, exon 12 | SEQ ID NO.: 17 |
| rhGALC coding sequence, exon 13 | SEQ ID NO.: 18 |
| rhGALC coding sequence, exon 14 | SEQ ID NO.: 19 |
| rhGALC coding sequence, exon 15 | SEQ ID NO.: 20 |
| rhGALC coding sequence, exon 16 | SEQ ID NO.: 21 |
| rhGALC coding sequence, exon 17 | SEQ ID NO.: 22 |
| rhGALC targeting vector | SEQ ID NO.: 23 |
| GALC c.G809A/c.T1637C cDNA, including intron 2 sequence | SEQ ID NO.: 24 |

In order to ensure germ line transmission it is further preferred that the said nucleic acid construct is inserted in the genome of said non-human mammal cell.

In further embodiments according to the invention, said nucleic acid construct disrupts an endogenous galactocerebroside-beta-galactosidase allele of said non-human mammal cell. In particular, the nucleic acid construct may be inserted into the genome of said non-human mammal by homologous recombination.

Optionally transcription of the recombinant GALC gene may be controlled by the endogenous GALC promoter.

In preferred embodiments the nucleic acid construct is inserted in exon 1 of an endogenous GALC gene in said non-human mammal cell, at the position of the endogenous translation initiation site. In order to keep all potential regulatory elements driving expression of the Galc gene, the endogenous genomic sequence downstream of exon 1 may also be left intact. According to these embodiments endogenous GALC protein is expected to be no longer expressed, due to termination of transcription at the inserted 3'UTR downstream of the human cDNA.

It is further within the scope of the invention to provide a pluripotent or totipotent non-human mammalian cell in which the recombinant GALC gene is generated from a full length GALC cDNA in which glycine has been changed to aspartic acid and isoleucine has been changed to threonine as defined above. Optionally, one or more intronic sequences from GALC genomic DNA may be introduced between the cDNA sequences derived from any two consecutive exons in the genomic GALC sequence. For instance, a sequence from the $1^{st}$ intron may be inserted into the nucleic acid construct between the sequences derived from the $1^{st}$ and the $2^{nd}$ exons between and/or a sequence from the $2^{nd}$ intron may be inserted into the nucleic acid construct between the sequences derived from the $2^{nd}$ and the $3^{rd}$ exons and/or a sequence from the $3^{rd}$ intron may be inserted into the nucleic acid construct between the sequences derived from the $3^{rd}$ and the $4^{th}$ exons, and so forth.

Preferably, the recombinant GALC gene is generated from a full length human GALC cDNA as defined by SEQ ID NO: 1. In specific embodiments, the GALC gene comprises the sequence from exons 1 through 17, as defined in SEQ ID NOs: 6-22 in consecutive order, with intronic sequence inserted between at least two of the exonic sequences in order to enhance transgene expression. Preferably, the nucleic acid sequence of the $2^{nd}$ intron of the human GALC gene is inserted between the sequences from exons 2 and 3. The $2^{nd}$ intron is preferred as this is the shortest intron in the human GALC gene.

In further preferred embodiments a Galc 3' untranslated region (UTR) has been inserted in the recombinant GALC gene downstream of the STOP codon in the sequence of exon 17. The UTR is inserted in order to improve expression of the recombinant GALC cDNA in non-human mammalian cells, such as mouse cells. According to these embodiments, endogenous GALC protein is expected to be no longer expressed, due to termination of transcription at the inserted 3'UTR downstream of the recombinant cDNA.

As the skilled person will understand, the pluripotent or totipotent non-human mammal cell according to the invention may either be heterozygous or homozygous for said recombinant GALC gene.

The pluripotent or totipotent non-human mammal cell according to the invention may be galactocerebroside-beta-galactosidase (GALC) deficient. As the skilled person will realize, GALC deficiency may be caused by reduced expression of the GALC gene and/or by reduction in the specific enzymatic activity of the enzyme. In the present context, "GALC deficiency" refers to situations where GALC activity in said cell is reduced to 5-60%, such as in the range of 5-50%, for example 5-40%, such as 10-40%, for example 15-40%, such as 15-30% of that in a pluripotent or totipotent cell from the same non-human mammalian species, which is homozygous for the wild-type GALC gene.

In further embodiments according to the invention, the galactocerebroside-beta-galactosidase (GALC) deficiency is inducible.

For the purpose of the present invention it is preferred that the non-human mammal cell is a pluripotent or totipotent mouse cell.

The non-human mammal cell is preferably a mouse embryonic stem (ES) cell. In particular, the non-human mammal cell may be a stem (ES) cell derived from the 129 mouse strain, or preferably from the C57BL/6 mouse strain. Each of the two cell type has advantages and disadvantages. C57BL/6 ES cells greatly facilitate the construction of targeting vectors since the genome of C57BL/6 mice has been completely sequenced and BAC clones spanning the entire genome are available. The sequences and sequence information are required for the cloning (or synthesis) of the murine 5'- and 3'-homology regions as well as the 5'- and 3'-untranslated regions of the targeting vector. Strain-specific sequence variations exist and prevent efficient recombination if C57BL/6 sequences are used for 129 ES cells or vice versa. Therefore, to accelerate the construction of the vector, C57BL/6 ES cells are preferred at present.

The disadvantage of C57BL/6 ES cells is, that they are more difficult to culture, that the chimera formation is less efficient and that the use of co-isogenic blastocysts is important. A novel C57BL/6 albino strain is available for coat colour screening. Since the technology for homologous recombination was first established for 129 ES cells, C57BL/6 ES cells are barely used by academic working groups.

Due to the preference for C57BL/6 ES cells it is also preferred that the non-human mammal cell comprises a nucleic acid sequence as set forth in SEQ ID NO: 23. The said nucleic acid sequence is a targeting vector specifically developed for use in embryonic stem cells derived from the C57BL/6 mouse strain.

A second aspect of the invention provides a method of making a genetically modified non-human mammal comprising the steps of
(a) providing a pluripotent or totipotent non-human mammal cell as defined above,
(b) inserting said pluripotent or totipotent non-human mammal cell into isolated blastocytes of said non-human mammal as defined above,
(c) implanting said blastocytes comprising said pluripotent or totipotent non-human mammal in a pseudopregnant female of said non-human mammal, and
(d) identify germline transmission in offspring of the pregnant female of step (c).

In particular embodiments of the invention, the said non-human mammal is a mouse, such as a mouse of the 129 mouse strain or preferably of the C57BL/6 strain.

Accordingly, it is also preferred that said non-human mammal cell is a mouse embryonic stem cell, such as a stem cell derived from the 129 mouse strain or preferably from the C57BL/6 strain.

According to further embodiments, the method involves measuring chimerism in chimeras (G0) by coat colour contribution of ES cells to the BALB/c host (black/white). The method may further comprise breading highly chimeric male offspring to strain C57BL/6 females. In these embodiments the C57BL/6 mating partners may be non-mutant (W) or mutant for the presence of a recombinase gene (Flp-Deleter or Cre-deleter or CreER inducible deleter or combination of Flp-deleter/CreER). The method may further involve identification of germline transmission by the presence of black, strain C57BL/6, offspring (G1).

A third aspect of the invention provides a galactocerebrosid-beta-galactosidase (GALC) deficient genetically modified non-human mammal comprising at least one exogenous nucleic acid construct encoding galactocerebroside-beta-galactosidase (GALC), wherein the amino acid corresponding to Glycine at position 270 in human GALC is changed to aspartic acid and the amino acid corresponding to isoleucine at position 546 in human GALC is changed to threonine.

In the context of the present invention, it is preferred that said exogenous nucleic acid construct encodes a galactocerebroside-beta-galactosidase, wherein glycine at position 270 (Gly270) is changed to aspartic acid and isoleucine at position 546 (Ile546) is changed to threonine.

In specific embodiments, the said exogenous nucleic acid construct comprises the sequence from exons 1 through 17, as defined in SEQ ID NOs: 6-22 in consecutive order, with intronic sequence inserted between at least two of the exonic sequences in order to enhance transgene expression. Preferably, the nucleic acid sequence of the $2^{nd}$ intron of the human GALC gene is inserted between the sequences from exons 2 and 3.

In further embodiments said galactocerebroside-beta-galactosidase comprises a sequence, which is essentially identical to the sequence set forth in SEQ ID NO: 3. In other embodiments the said galactocerebroside-beta-galactosidase comprises or consists essentially of the sequence set forth in SEQ ID NO: 3.

Preferably, said galactocerebroside-beta-galactosidase consists of a sequence, which is identical to the sequence set forth in SEQ ID NO: 3.

In still further embodiments the genetically modified non-human mammal according to the invention is one wherein said exogenous nucleic acid construct encodes a human galactocerebroside-beta-galactosidase (GALC).

According to other embodiments, the genetically modified non-human mammal according to the invention comprises at least one exogenous nucleic acid construct encoding a human galactocerebroside-beta-galactosidase, wherein said galactocerebroside-beta-galactosidase comprises a sequence, which is essentially identical to the sequence set forth in SEQ ID NO: 3.

In currently preferred embodiments the genetically modified non-human mammal according to the invention is one wherein said galactocerebroside-beta-galactosidase comprises the sequence set forth in SEQ ID NO: 3.

In equally preferred embodiments, the said exogenous nucleic acid construct comprises a nucleic acid sequence, which is essentially identical to the sequence set forth in SEQ ID NO.: 1. Again, when used in the present context, the term "essentially identical" is to be construed broadly so as to include nucleic acid sequences in which the sequence set forth in SEQ ID NO.: 1 has been modified, such as by insertion, deletion and/or substitution of one or more nucleic acid residues, provided that transcription of the nucleic acid sequence and subsequent translation of the transcription product results in a galactocerebroside-beta-galactosidase which has the amino acid sequence set forth in SEQ ID NO: 2.

In order to obtain germ line transmission the genetically modified non-human mammal according to the invention may be one, wherein said recombinant gene is inserted in the genome of said non-human mammal cell.

It is also preferred that the genetically modified non-human mammal according to any of the invention is one wherein said recombinant gene disrupts an endogenous galactocerebroside-beta-galactosidase allele of said non-human mammal cell, as would serve as a means for preventing expression of endogenous galactocerebroside-beta-galactosidase.

As mice, due to their size and frequent alternations of generations, would be the preferred animal model for studies on GLD it is preferred that the non-human mammal according to the invention is a mouse.

Particular embodiments of the invention provide a genetically modified mammal, which is immune tolerant to the galactocerebrosid-beta-galactosidase (GALC) enzyme encoded by said exogenous nucleic acid construct.

In further embodiments of the invention the galactocerebrosid-beta-galactosidase (GALC) deficiency in said genetically modified non-human mammal is inducible.

More specifically, the galactocerebrosid-beta-galactosidase (GALC) deficiency in said genetically modified non-human mammal may only be present in adult animals.

According to particular embodiments of the invention, globoid cell leukodystrophy manifests itself, and the genetically modified non-human mammal starts developing symptoms of at the time of weaning or some time thereafter. The particular point in time when globoid cell leukodystrophy manifests itself and the symptoms start to appear depend on the animal species; in the presently preferred embodiments according to which the animal is a mouse, the symptoms may appear when the mice are approximately 20 days of age, such as from 15 to 30 days of age, such as from 15-25 days of age, from 15-22 days of age, from 18-30 days of age, from 18-25 days of age, from 18-22 days of age or such as from 19-22 days of age.

Generally, early symptoms of GLD include hypersensitivity to auditory, tactile or visual stimuli, fever, stiffness, seizures, feeding difficulties, vomiting, and slowing of mental and motor development. Later symptoms include muscle weakness, spasticity, deafness, optic atrophy and blindness, paralysis, and difficulty when swallowing. In mice, behavioural symptoms of GLD typically include tremor, compromised motor functions and hind limb paresis.

In particular embodiments according to the invention the homozygous humanised mice start to gain less weight than heterozygous or wild-type mice at 20-22 days of age. According to these embodiments, first signs of tremors and twitching are observed and progressive hind leg weakness appears at 26-32 days of age. According to these embodiments, reduced cage motility appears at 34-50 days of age.

The genetically modified non-human mammal according to any of the preceding claims, where overt globoid cell leukodystrophy onsets at the age of 15 to 50 days of age, such as approximately 20 days of age, such as from 15 to 30 days of age, such as from 15-25 days of age, from 15-22 days of age, from 18-30 days of age, from 18-25 days of age, from 18-22 days of age or such as from 19-22 days of age.

A third aspect of the invention provides use of the genetically modified non-human mammal according to the invention for screening and/or validation of an agent useful as a medicament for treatment and/or prevention of globoid cell leukodystrophy. In particular, the screening and/or validation process may combine biochemical, electrophysiological, histological and behavioural evaluations, including:
  i) Determination of accumulation of psycosin in the central nervous system and in the peripheral nervous system
  ii) Determination of any effect on motor functions
  iii) Disappearance of globoid cells.

In particular, the use according to the invention may involve determination of pharmacokinetics, pharmacodynamics, ADME (absorptioin, distribution, metabolism and excretion), toxicity and possible side effects of single dosing of said agent. In addition the use may involve analysis at different time points after dosing in order to determine the time-dependency of therapeutic effects Also, the use according to the invention may involve repeated injection of the agent for instance in order to optimize dosage regimen, including dosage size and administration intervals and/or to evaluate possible side effects, including immunological side effects, of repeated treatment. The use according to the invention may also involve long-term studies to evaluate the full therapeutic potential of administration of said agent.

Due to uptake by recipient cells via mannose 6-phosphate dependent endocytosis and lysosomal delivery of extracellular galactocerebrosid-beta-galactosidase, enzyme replacement therapy (ERT) may be a therapeutic option for Krabbe disease. Hence, in particular embodiments the said agent is an isolated recombinant galactocerebrosid-beta-galactosidase (GALC).

According to additional embodiments the agent is an isolated recombinant human galactocerebrosid-beta-galactosidase (GALC).

A fourth aspect of the invention provides a method of validating an agent comprising the steps of:
  a) providing a genetically modified non-human mammal as described above,
  b) contacting said non-human mammal with an agent for validation,
  c) determining whether said non-human mammal is responsive to said agent after said contact.

In particular embodiments the said agent is isolated recombinant galactocerebrosid-beta-galactosidase (GALC).

According to additional embodiments the agent is isolated recombinant human galactocerebrosid-beta-galactosidase (GALC).

The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. Furthermore, individual features mentioned in different claims, may possibly be advantageously combined, and the mentioning of these features in different claims does not exclude that a combination of features is not possible and advantageous.

In the following, the invention will be illustrated by way of examples which are not in any way intended to limit the scope of protection.

EXAMPLES

Example 1: Generation of Immunotolerant Mouse Model for Krabbe Disease

Experimental Strategy and Design of the Knockin Targeting Vector

The experimental strategy involved removal of the 57 kb coding region of the GALC gene from chromosome 12 of the mouse genome and substitution with a human full length GALC cDNA harbouring the mutation c.G809A (p.G270D) and the polymorphism c.T1637C (p.I546T). The expression of the inserted mutant human GALC cDNA was to be controlled by the endogenous murine GALC promoter and poly(A) signal.

The genomic sequence upstream from the coding region, the 5'-untranslated region and the 3'-untranslated region of the murine gene was to remain untouched. The ATG start codon and TAA stop codon of the human cDNA was to be positioned exactly onto the murine ATG and TAA codon, respectively. To increase transgene expression rates the second intron of the human GALC gene (247 bp) would be incorporated into the human GALC cDNA.

To enable homologous recombination in embryonic stem (ES) cells a ~10 kb long 5'-sequence which is homologous to the genomic sequence upstream from the murine GALC gene was added to the targeting vector (long homology arm). Likewise, a ~1.8 kb long 3'-sequence which is homologous to the genomic sequence downstream from the murine GALC gene was added (short homology arm). In an alternative approach, the length of the long homology arm was approximately 6 kb, while the length of the short homology arm was approximately 4 kb.

For this purpose, a vector backbone harbouring all modules except the murine 5'-homology region was generated by de novo synthesis. This vector contained two unique restriction sites which allowed for the subsequent insertion of the murine 5'-homology region. The murine 5'-homology region was obtained by PCR-amplification using C57BL/6-derived genomic DNA or BAC clones as a template. Alternatively, the sequence was retrieved by recombineering from a BAC clone encompassing the 5' region of the murine GALC gene. Subsequently, the 5'-homology region was inserted into the vector backbone.

A neomycin resistance cassette was incorporated into the targeting vector to enable positive selection of ES cell clones in which the vector has been stably genomically integrated. In an alternative approach, a puromycin resistance marker was used for positive selection. The resistance cassette was flanked by FRT-sites to allow the excision of the cassette after generation of transgenic mice via a Flip recombinase. Removal of the selection marker is required to reduce the risk of interference between the SV40 promoter of the neomycin resistance cassette and the murine GALC promoter.

For negative selection of ES cell clones with random integration, a second expression cassette encoding the diphtheria toxin alpha subunit was added to the 3' end of the vector sequence. This cassette lacked a poly(A) signal. Due to the lack of polyadenylation, transcripts were unstable and no protein could be translated before the vector is genomically integrated. After random integration into the genome, the cellular RNA polymerase transcribed the open reading frame until it recognized a functional poly(A) signal in the genomic sequence downstream from the random integration site. The mRNA was stabilized by polyadenylation and diphtheria toxin alpha subunit was expressed so as to kill the cell. When the vector integrated site-specifically via homologous recombination, the expression cassette got lost and no toxic product could be expressed. In an alternative approach, a thymidine kinase expression cassette was included for negative selection of random integrants.

To allow for a future exchange of sequence modules from the targeting vector, unique restriction sites was inserted at positions at which sequence modifications would not interfere with vector function. The vector was flanked by unique EcoRV sites which (i) allowed for the construction of the vector backbone by de novo DNA synthesis in standard vectors like pBluescript and (ii) the excision of the targeting vector from plasmids. The total length of the targeting vector construct did not exceed 18 kb.

In summary, the vector design was as follows: 5'-[murine 5'-homology region, 10 kb]-[human mutated GALC cDNA with intron 2, 2.2 kb]-[murine 3'-UTR with poly(A), 1.6 kb]-[murine 3'-flanking region as spacer, 0.15 kb]-[frt-flanked neomycin resistance cassette, 1.4 kb]-[murine 3'-homology region, 1.8 kb]-[diptheria toxin subunit alpha expression cassette, 1.6 kb]-3'. FIG. 1 shows a graphic representation of the vector design. The nucleic acid sequence of the targeting vector is set forth in SEQ ID NO: 23.

ES Cell Culture and Homologous Recombination

C57BL/6N ES cells were grown on a mitotically inactivated feeder layer of mouse embryonic fibroblasts in DMEM high-glucose medium containing 20% fetal bovine serum (PAN-Biotech, Aidenbach, Germany) and 1200 U/mL leukemia inhibitory factor (ESG 1107; Millipore, Schwalbach, Germany). Cells ($1 \times 10^7$) were electroporated with linearized vector DNA (30 μg) using a Bio-Rad Gene Pulser (Bio-Rad, Munich, Germany) at 240 V and 500 μF. Puromycin selection (1 μg/mL) was started on day 2, counterselection with gancyclovir (2 μM) on day 5 after electroporation. Selected ES clones were isolated on day 8 and analyzed by Southern blotting according to standard procedures using appropriate restriction enzymes and internal and external probes. Correct homologous recombination and single integration was validated in 12 of 145 ES cell clones indicating a targeting frequency of 8.3% (not shown).

Example 2: Production of Chimeric Mice

Blastocysts were isolated from superovulated BALB/c females at dpc 3.5. For microinjection, blastocysts were placed in a drop of DMEM with 15% FCS under mineral oil. A flat tip, piezo actuated microinjection pipette with an internal diameter of 12-15 μm was used to inject 10-15 targeted C57BL/6NTac ES cells into each blastocyst. A total of 98 blastocysts was injected with ES cells from two targeted clones. After recovery, 8 injected blastocysts were transferred to each uterine horn of 2.5 days post coitum, pseudopregnant NMRI females. The foster mice gave birth to 29 pups of which 18 were chimeras. Chimerism was determined by coat colour contribution of ES cells to the BALB/c host (black/white). Five highly chimeric male mice (>50%) were bred to C57BL/6 females being transgenic for the Flp recombinase gene (Schaft et al., 2001). Two breeding pairs produced a total of 96 pups. Germline transmission was identified by the presence of black, strain C57BL/6, offspring. Mice heterozygous for the humanized GALC allele were identified by PCR genotyping and crossed to generate homozygous offspring.

Genotyping PCR

Detection Heterozygous and Homozygous Humanized Alleles.

Primers:

```
2282_45:
GCATGGAAGTGACAGGATGC,

2282_46:
AATATCCCAGATCGCTTCAGG

1260_1:
GAGACTCTGGCTACTCATCC,

1260_2:
CCTTCAGCAAGAGCTGGGGAC
```

Reaction:
  5 µl PCR Buffer 10× (Invitrogen), 2 µl MgCl2 (50 mM), 1 µl dNTPs (10 mM), 1 µl Primer 2282_45 (5 µM), 1 µl Primer 2282_46 (5 µM), 1 µl Primer 1260_1 (5 µM) 1 µl Primer 1260_2 (5 µM), 0.2 µl Taq (5 U/µl, Invitrogen), 35.8 µl H2O, 2 µl DNA.
Program:
1 X 95° C. 5 min
35 cycles: 95° C. 30 sec, 60° C. 30 sec, 72° C. 1 min
1 X 72° C. 10'
Expected Fragments [bp]: 474(hum)
Expected Control Fragments [bp]: 585(c)

The fragment amplified with oligos 1 (2282_45: GCATGGAAGTGACAGGATGC)+2 (2282_46: AATATCCCAGATCGCTTCAGG) detected heterozygous and homozygous humanized alleles. Applying the conditions described above would not allow detection of the wildtype allele of Galc. The zygosity of the humanized allele was verified by applying the procedure below for detection of heterozygous and homozygous wildtype alleles. The amplification of the positive control fragment (585 bp (c)) by using oligos 1260_1 and 1260_2 referred to the CD79b wildtype allele (NT_165773.2 nt 17714036-17714620 Chr.11) for testing the integrity of the PCR sample.

Detection of Heterozygous and Homozygous Wildtype Alleles.
Primers:

```
2283_48
CGTCTGCTGCAGTCAAGTGG,

2282_46:
AATATCCCAGATCGCTTCAGG

1260_1:
GAGACTCTGGCTACTCATCC,

1260_2:
CCTTCAGCAAGAGCTGGGAC
```

Reaction
  5 µl PCR Buffer 10× (Invitrogen), 2 µl MgCl2 (50 mM), 1 µl dNTPs (10 mM), 1 µl Primer 2283_48 (5 µM), 1 µl Primer 2282_46 (5 µM), 1 µl Primer 1260_1 (5 µM), 1 µl Primer 1260_2 (5 µM), 0.2 µl Taq (5 U/µl, Invitrogen), 35.8 µl H2O, 2 µl DNA.
Program:
1 X 95° C. 5 min
35 cycles: 95° C. 30 sec, 60° C. 30 sec, 72° C. 1 min
1 X 72° C. 10'
Expected Fragments [bp]: 316(W)
Expected Control Fragments [bp]: 585(c)

The fragment amplified with oligos 3 (2283_48: CGTCTGCTGCAGTCAAGTGG)+2 (2283_46: AATATCCCAGATCGCTTCAGG) detected heterozygous and homozygous wildtype alleles. The amplification of the positive control fragment (585 bp (c)) by using oligos 1260_1 and 1260_2 referred to the CD79b wildtype allele (NT_165773.2 nt 17714036-17714620 Chr.11) for testing the integrity of the PCR.

Detection of the Flp Transgene
Primers:

```
1307_1:
Flpe_as_GGCAGAAGCACGCTTATCG,

1307_2:
Flpe_s_GACAAGCGTTAGTAGGCACAT
```

Reaction:
  5 µl PCR Buffer 10× (Invitrogen), 2 µl MgCl2 (50 mM), 1 µl dNTPs (10 mM), 1 µl Primer 1307_1 (5 µM), 1 µl Primer 1307_2 (5 µM), 0.2 µl Taq (5 U/µl, Invitrogen), 37.8 µl H2O, 2 µl DNA.
Program:
1 X 95° C. 5 min
35 cycles: 95° C. 30 sec, 60° C. 30 sec, 72° C. 1 min
1 X 72° C. 10'
Expected Fragments [bp]:343(targ)

Detection of the Flp transgene, inclusion of 1307+Control to create an additional control fragment at 585 bp (PCR-ID 1260)
Primers:

```
1307_1:
Flpe_as_GGCAGAAGCACGCTTATCG,

1307_2:
Flpe_s_GACAAGCGTTAGTAGGCACAT,

1260_1:
GAGACTCTGGCTACTCATCC,

1260_2:
CCTTCAGCAAGAGCTGGGAC
```

Reaction:
  5 µl PCR Buffer 10× (Invitrogen), 2 µl MgCl2 (50 mM), 1 µl dNTPs (10 mM), 1 µl Primer 1307_1 (5 µM), 1 µl Primer 1307_2 (5 µM), 1 µl Primer 1260_1 (5 µM), 1 µl Primer 1260_2 (5 µM), 0.2 µl Taq (5 U/µl, Invitrogen), 35.8 µl H2O, 2 µl DNA.
Program:
1 X 95° C. 5 min
35 cycles: 95° C. 30 sec, 60° C. 30 sec, 72° C. 1 min
1 X 72° C. 10'
Expected Fragments [bp]: 343(targ)
Expected Control Fragments [bp]: 585(c)

Example 3: Pathophysiological Analysis of Humanized Knock-in Mice

Parameters

The analysis of mice which are homozygous for the human mutant GALC allele hGALC$^{G809A/T1637C}$ can be divided into five parts: analysis of general phenotype, biochemical validation, analysis of general phenotype, evaluation of biochemical disease markers and evaluation of histological disease markers (see list below). It has to be mentioned that results of some investigations determine the details of successive analyses. If behavioural abnormalities are undetectable, for example, electrophysiological measurements of nerve conduction will be omitted. The following list therefore represents a collection of possible analyses which make sense considering that humanized knockin mice develop a mild variant of the twitcher phenotype with increased life span but overt behavioral deficits. Analyses which are obligatory to evaluate the phenotype and which will be done also in the absence of an overt phenotype are underlined. Methods are indicated in brackets.

(1) General Phenotype
   mortality
   weight
   behaviour (tremor, motor functions, hind limb paresis)
(2) Biochemical Validation of Genetic Modification
   determination of residual GALC activity (activity assays)
   analysis of human GALC mRNA (Northern blotting)
   analysis of human GALC polypeptide (Western blotting)
   expression pattern of human GALC (in situ hybridization, immunohistochemistry)
   evaluation of GALC activity in situ (X-Gal staining)
(3) Analysis of General Phenotype
   mortality, life expectancy (Kaplan-Meier survival curves)
   postnatal weight gain (regular weight determination)
   behavior, age-dependent
      tremulousness (visual inspection)
      motor functions (rotarod)
      exploratory activity (open field, elevated plus maze)
      gait pattern (treadmill)
      swimming velocity (automized tracking system)
   electrophysiology (analysis of compound motor action potentials)
(4) Evaluation of Biochemical Disease Markers
   lipid profiling (thin layer chromatography, ESI-MS)
   quantification of psychosine and galactosylceramide (TLC, ESI-MS)
   analysis of astrogliosis marker GFAP (Western blotting)
   analysis of inflammation markers e.g. IL-1α, IL-1β, IL-2, IL-3, IL-4, IL-5, IL-6, IL-10, IL-17, IFNα, IFNβ, IFNγ, IL-6, TNFα, MIP1α, MIP1β, MCP-1, RANTES, CXCR4, CCR7, MHC-I, MHC-II, Iba-1, CD11b, CD68, CD4, CD8 (qPCR, protein chips, Western, Northern blotting)
   analysis of myelin markers e.g. MBP, PLP, MAG (Western blotting)
(5) Evaluation of Histological Disease Markers
   general histology (HE-staining)
   detection of globoid cells (PAS-staining)
   macrophage infiltration (lectin staining)
   apoptosis (apoptosis detection kits)

Larger groups comprising age-matched homozygous mice of e.g. three different ages (e.g. 1, 3 and 6 months old) are analysed in parallel to get comprehensive and statistical relevant data. Age-matched wild type mice with the same genetic background are used as negative controls. Twitcher mice may be used as positive controls.

Preliminary Results

Figure 2:
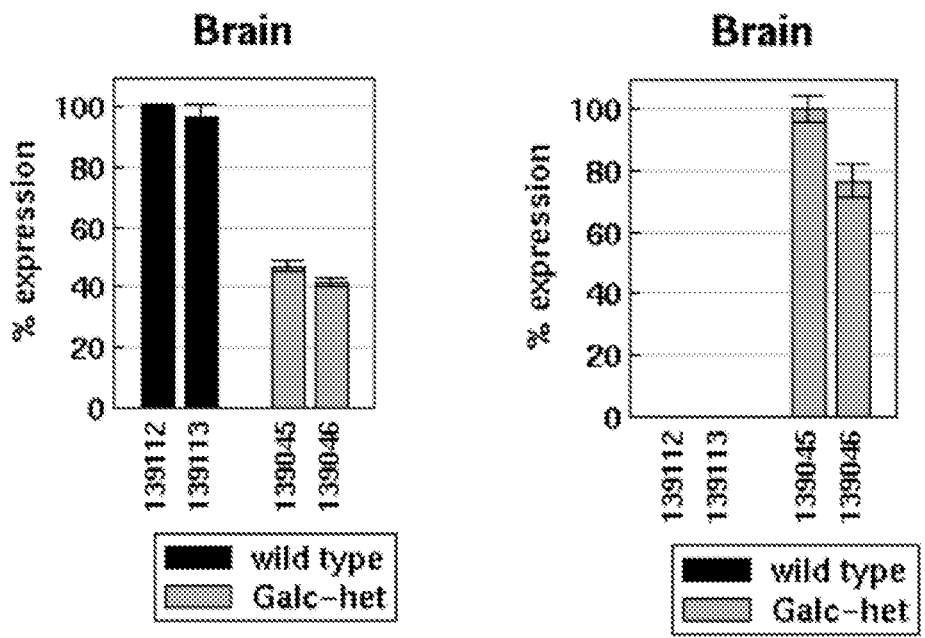
FIG. 2: Phenotype of heterozygous hGALC$_{mut}$ knockin mouse. A: Expression of mouse GALC mRNA in brain, B: expression of human GALC mRNA in brain, C: levels of human vs. murine GALC mRNA in various organs.
Figure 2:
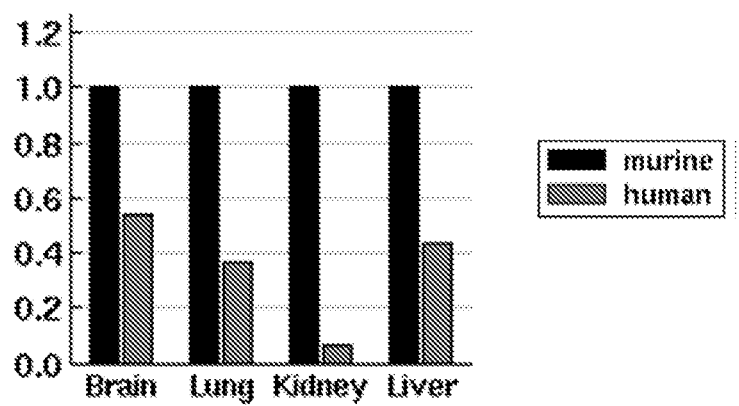
Figure 3:
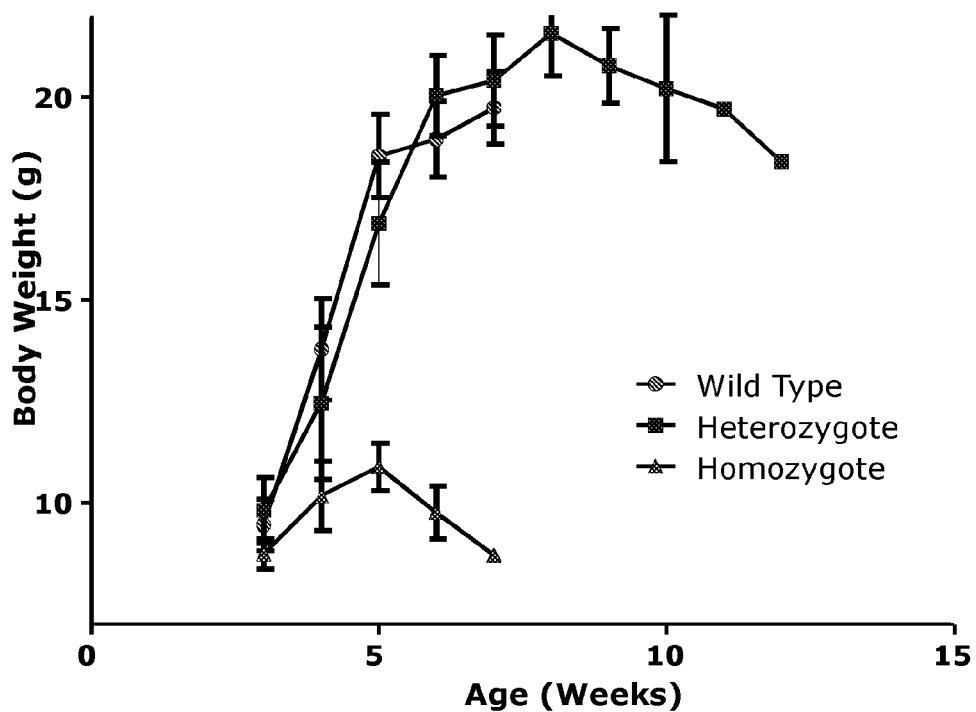
FIG. 3: Body weight of mice over time (weeks). Wildtype mice, heterozygous hGALC$_{mut}$ knockin mice and homozygous hGALC$_{mut}$ knockin mice.

Heterozygous knockin mice have no obvious disease phenotype. Results from analysis of expression of human GALC$_{mut}$ mRNA and murine GALC mRNA as determined by real-time PCR with TaqMan probes is shown in FIG. 2. The studies showed that 7-53% of human GALC is expressed in the heterozygous mice compared to murine GALC.

Observations on the Phenotype of Homozygous Knock-in Mice

Homozygous knock-in mice display a clinical course of GLD comparable to twitcher mice. Beginning Beginning in the fourth week of age, the homozygous humanized mice start to gain less weight than heterozygous or wild type mice. Total body weights were low (Table 4), but slightly higher than those reported for twitcher mice. Between PND 26-32 (average 30.1) first signs of tremors and twitching were observed, and progressive hind leg weakness started to appear, and between PND 34-50 (average 40.4) reduced cage motility was noted. The average lifespan of 14 observed animals was 45.8±7.3 days (mean±SD). This life expectancy is somewhat longer than that reported for the twitcher mouse (40 d).

TABLE 4

Body weight of wild type and transgenic mice

| Genotype | Body weight |
|---|---|
| wt/wt | 18.4 g |
| tg/wt | 20.5 g |
| tg/tg | 5.2 g |

The level of GALC activity was determined in wild type mice, homozygous mice and hereozygous mice. Results are shown in table 5 below.

TABLE 5

Levels of GALC activity in wild type, homozygous and hereozygous mice

Figure 4:
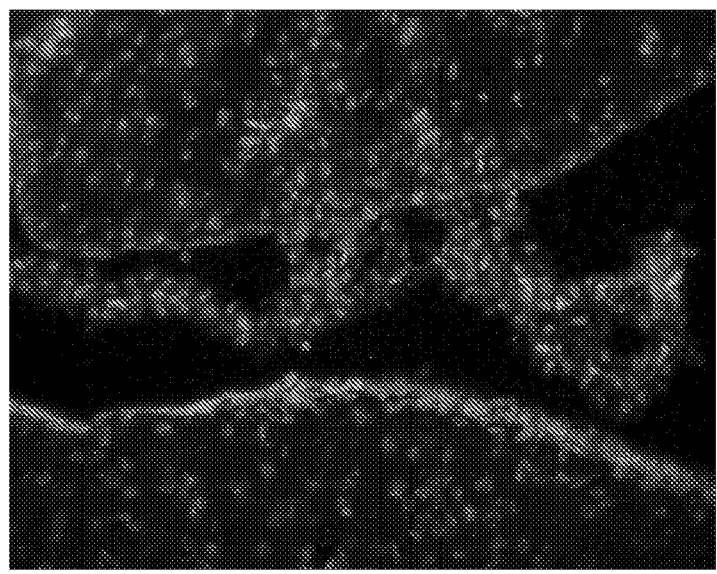
FIG. 4: rhGALC in the Brain (choroid plexus) as determined by immunohistochemistry (20×1 sec) with pabGALC (red) and labeling of Nuclei with DAPI (blue).
Figure 4:
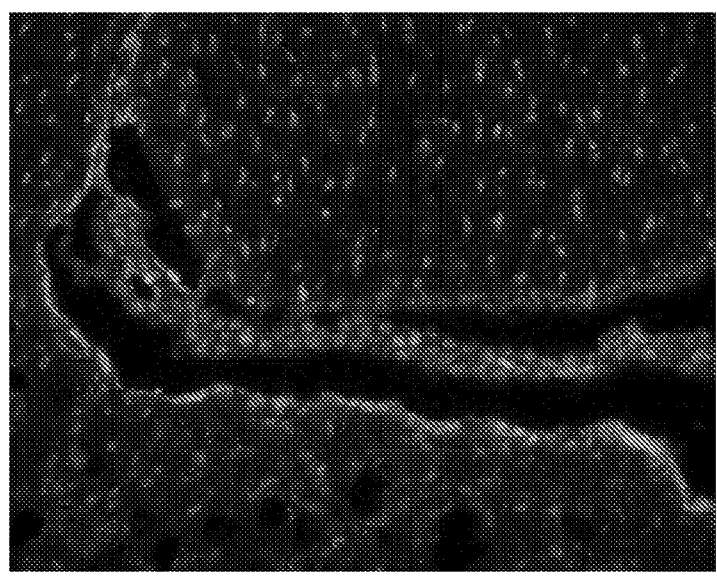

|  | Animal | Brain | Heart | Liver | Kidney (L) | S.C. |
|---|---|---|---|---|---|---|
| WT | 46/27/6/2m | 2.50 | 0.24 | 0.86 | 6.60 | 1.50 |
|  | 77/20/15m | 2.50 | 0.27 | 1.50 | 7.20 | 1.70 |
|  | Average | 2.50 | 0.26 | 1.18 | 6.90 | 1.60 |
| Homoz | 46/27/6/1m | 0.05 | 0.15 | 0.21 | 0.09 | 0.00 |
|  | 46/27/6/2m | 0.12 | 0.00 | 0.12 | 0.17 | 0.03 |
|  | 46/27/6/6f | 0.13 | 0.12 | 0.23 | 0.07 | 0.17 |
|  | Average | 0.10 | 0.09 | 0.19 | 0.11 | 0.07 |
| Heteroz | 46/27/6/4m | 0.67 | 0.14 | 0.55 | 3.80 | 0.75 |
|  | 46/27/6/5f | 0.88 | 0.10 | 1.20 | 3.70 | 0.83 |
|  | 46/27/6/7f | 1.50 | 0.29 | 0.77 | 3.60 | 0.86 |
|  | Average | 1.02 | 0.18 | 0.84 | 3.70 | 0.81 | rhGALC in the Brain (choroid plexus) was determined by immunohistochemistry (20 × 1 sec) with pabGALC (red) and labeling of Nuclei with DAPI (blue). Results are shown in FIG. 4.

Example 4: Immunological Tolerance to Recombinant Human GALC

Figure 5:
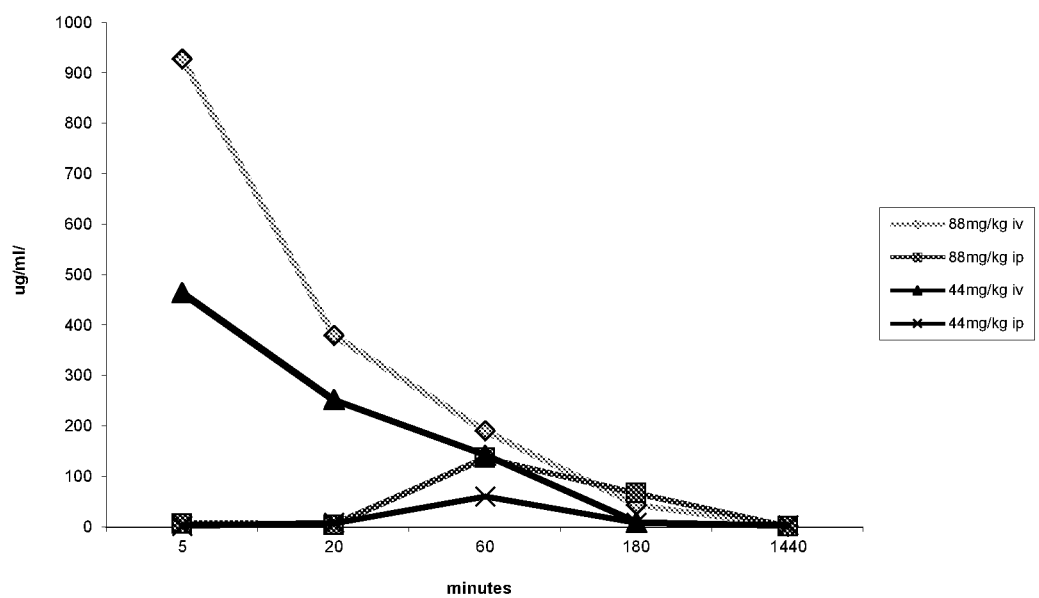
FIG. 5: Circulating levels of recombinant human GALC in blood in homozygous hGALC$_{mut}$ knockin mice after intravenous and intraperitoneal injection.

Transgenic expression of mutant human GALC in the novel humanized mouse model of globoid cell leukodystrophy was expected to confer immunological tolerance to intravenously injected rhGALC, allowing for long-term ERT trials without immunological side-effects. To test this notion, recombinant human GALC was administered, either by intravenous infusion of into the tail vein or by intraperitoneal injection into hGALC$^{G809A/T1637C}$ homozygous mice. Circulating levels of recombinant human GALC in blood after intravenous and intraperitoneal injection are shown in FIG. 5.

Figure 6:
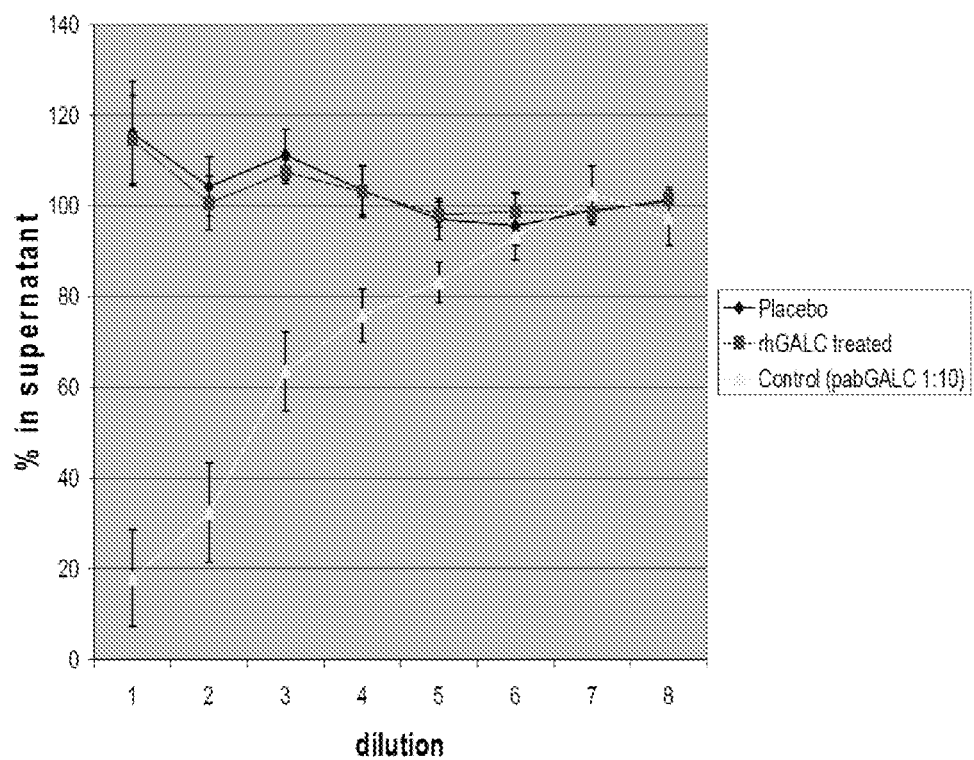
FIG. 6: Antibody titers in dosed homozygous hGALC$_{mut}$ knockin mice.

In order to confirm that the mice are immunotolerant to administration of exogenous GALC, rhGALC was incubated with serum (8 dilution steps). Antibodies bound to rhGALC were precipitated after incubation with Pansorbin. The residual GALC activity in the supernatant was determined using the HNG activity assay. As shown in FIG. 6, no aGALC antibody titer was detected in the treated mice.

REFERENCES

R De Gasperi, V L Friedrich, G M Perez, E Senturk, P H Wen, K Kelley, G A Elder and M A Gama Sosa: Transgenic rescue of Krabbe disease in the twitcher mouse, Gene Therapy (2004) 11, 1188-1194. doi:10.1038/sj.gt.3302282 Published online 27 May 2004.

Paola Luzi, Mohammad A. Rafi, Mariam Zaka, Mark Curtis, Marie T. Vanier, and David A. Wenger, Generation of a Mouse with Low Galactocerebrosidase Activity by Gene Targeting: A New Model of Globoid Cell Leukodystrophy (Krabbe Disease), *Molecular Genetics and Metabolism*, Vol. 73, 3, July 2001, Pages 211-223.

Altschul S F, Gish W, Miller W, Myers E W, Lipman D J. Basic local alignment search tool. *J Mol Biol.* 1990 Oct. 5; 215(3):403-10 (PMID: 2231712).

Tappino B, Biancheri R, Mort M, Regis S, Corsolini F, Rossi A, Stroppiano M, Lualdi S, Fiumara A, Bembi B, Di Rocco M, Cooper D N, Filocamo M. Identification and characterization of 15 novel GALC gene mutations causing Krabbe disease. Hum Mutat. 2010 December; 31(12): E1894-914. (PMID: 20886637)

The invention claimed is:

1. A galactocerebroside-beta-galactosidase (GALC) deficient transgenic mouse having a genome comprising a homozygous disruption of the endogenous GALC gene, wherein the disruption comprises at least one exogenous nucleic acid construct encoding human GALC, wherein the amino acid corresponding to glycine at position 270 in human GALC as set forth in SEQ ID NO.: 4 is changed to aspartic acid and the amino acid corresponding to isoleucine at position 546 in human GALC as set forth in SEQ ID NO.: 4 is changed to threonine, wherein the transgenic mouse is GALC deficient, and wherein the transgenic mouse is a model for Krabbe's disease.

2. The transgenic mouse according to claim 1, wherein said human GALC comprises a sequence, which is at least 95%, 96%, 97%, 98%, 99%, 99.5% or 99.7% identical to the sequence set forth in SEQ ID NO.: 3.

3. The transgenic mouse according to claim 1, wherein said human GALC comprises the sequence set forth in SEQ ID NO.: 3.

4. The transgenic mouse according to claim 1, wherein said transgenic mouse is immune tolerant to the human GALC enzyme encoded by said exogenous nucleic acid construct.

5. The transgenic mouse according to claim 1, wherein said GALC deficiency is inducible.

6. A method of validating an agent for treatment of globoid cell leukodystrophy comprising:
   (a) providing the transgenic mouse according to claim 1,
   (b) contacting said mouse with an agent for validation, and
   (c) determining whether said mouse is responding to said agent after said contact, wherein said step of determining includes at least one of
      i) determining accumulation of psycosin in the central nervous system and in the peripheral nervous system in said mouse,
      ii) determining any effect on motor functions of said mouse, and
      iii) determining a disappearance of globoid cells in said mouse.

7. The method according to claim 6, wherein said agent is isolated recombinant GALC.

8. The method according to claim 7, wherein said agent is isolated recombinant human GALC.

* * * * *